US010761096B2

(12) United States Patent
Haney et al.

(10) Patent No.: US 10,761,096 B2
(45) Date of Patent: Sep. 1, 2020

(54) QUANTITATIVE PEPTIDE OR PROTEIN ASSAY

(71) Applicant: Pierce Biotechnology, Inc., Rockford, IL (US)

(72) Inventors: Paul Jeffrey Haney, Beloit, WI (US); Christopher L. Etienne, Oregon, WI (US); Sijian Hou, Rockford, IL (US); Erum Raja, Rockford, IL (US); Ramesh Ganapathy, Loves Park, IL (US)

(73) Assignee: Pierce Biotechnology, Inc., Rockford, IL (US)

( * ) Notice: Subject to any disclaimer, the term of this patent is extended or adjusted under 35 U.S.C. 154(b) by 62 days.

(21) Appl. No.: 16/299,667

(22) Filed: Mar. 12, 2019

(65) Prior Publication Data

US 2019/0195885 A1 Jun. 27, 2019

Related U.S. Application Data

(62) Division of application No. 15/674,831, filed on Aug. 11, 2017, which is a division of application No. 14/734,678, filed on Jun. 9, 2015, now abandoned.

(60) Provisional application No. 62/010,594, filed on Jun. 11, 2014.

(51) Int. Cl.
G01N 33/68 (2006.01)

(52) U.S. Cl.
CPC ..... *G01N 33/6833* (2013.01); *G01N 33/6839* (2013.01); *G01N 2560/00* (2013.01)

(58) Field of Classification Search
None
See application file for complete search history.

(56) References Cited

U.S. PATENT DOCUMENTS

| 4,839,295 | A | 6/1989 | Smith |
| 5,693,291 | A | 12/1997 | Strobel et al. |
| 6,613,577 | B1 | 9/2003 | Da Cruz |
| 2009/0197348 | A1 | 8/2009 | Mallia et al. |
| 2011/0073172 | A1 | 3/2011 | LeSuer et al. |
| 2015/0362504 | A1 | 12/2015 | Haney et al. |

OTHER PUBLICATIONS

Bainor, A. et al., "Bicinchoninic Acid (BCA) Assay in Low Volume," Analytical Biochemistry, 2011, 410(2):310-312.
Bradford. A Rapid and Sensitive Method for the Quantitation of Microgram Quantities of Protein Utilizing the Principle of Protein-Dye Binding. Analytical Biochemistry 72 (1976) 248-254.
Campos et al., "Evaluation of the Copper(II) Reduction Assay Using Bathocuproinedisulfonic Acid Disodium Salt for the Total Antioxidant Capacity Assessment: The CUPRAC-BCS Assay," Analytical Biochemistry, 2009, 392:37-44.

(Continued)

Primary Examiner — Xiaoyun R Xu
(74) Attorney, Agent, or Firm — McNeill Baur PLLC

(57) ABSTRACT

Peptide and/or protein quantitation methods, kits, and compositions, particularly useful for mass spectrometry, are provided herein based on a bathocuproine-based composition complex such as bathocuproinedisulfonic acid disodium salt hydrate complex. The methods are one-step rapid absorbance methods using small sample volumes. They produce a robust signal with high signal to background ratio and accurately quantitate even complex peptide mixtures with low variability and high sensitivity.

29 Claims, 16 Drawing Sheets

Specification includes a Sequence Listing.

Concentration (µg/mL) )480 nm/562 nm

(56) References Cited

OTHER PUBLICATIONS

Extended European Search Report received in European Patent Application No. 15806609.2, dated Sep. 28, 2017, 10 pages.
Gornall et al. Determination of Serum Proteins by Means of the Biruet Reaction. J. Biol. Chem. 177 (1949 751-766.
Ivanov, A.I. et al. Bathocuproine-assisted reduction of copper(II) by human albumin, 2000, JBIC, vol. 5, pp. 102-109.
Kapoor et al. Estimation of peptide concentration by a modified bicinchoninic acid assay. Analytical Biochemistry 393 (2009) 138-140.
Lowry et al. Protein Measurement with the Folin Phenol Reagent. J. Biol. Chem. 193 (1951) 265-275.
Martyshkin et al., "Fluorescence Assay for Monitoring Zn-Deficient Superoxide Dismutase In Vitro," Spectrochimica Acta Part A, 2003, 59:3165-3175.
Matsuhita et al. Determination of proteins by a reverse biuret method combined with copper-bathcuproine chelate reaction. Clinica Chimica Acta 216 (1993) 103-111.
Rapisarda et al., "Quenching of Bathocuproine Disulfonate Fluorescence by Cu(I) as a Basis for Copper Quantification," Analytical Biochemistry, 2002, 307:105-109.
Sapan et al., "Colorimetric Protein Assay Techniques," Biotechnol. Appl. Biochem., 1999, 29:99-108.
Shen et al., "An IonStar Experimental Strategy for MS1 Ion Current-Based Quantification Using Ultra-High-Field Orbitrap: Reproducible, In-Depth and Accurate Protein Measurement in Larger Cohorts," J Proteome Res., 2017, 1-36.
Shimada et al., "Photoassisted Electrochemical Deposition of Copper from a Bathocuproin Complex," Japanese Journal of Applied Physics, 2003, 42:L964-966.
Smith et al. Measurement of Protein Using Bicinchoninic Acid. Analytical Biochemistry 150 (1985) 76-85.
Sözgen et al. Spectrophotometric total protein assay with copper(II)-neocuproine reagent in alkaline medium. Talanta 68 (2006) 1601-1609.
Stoscheck. Protein Assay Sensitive at Nanogram Levels. Analytical Biochemistry 160 (1987) 301-305.
International Search Report and Written Opinion PCT/US15/34960 dated Sep. 2, 2015, 8 pages.
Zhu et al. Quantification of Proteins by Functionalized Gold Nanoparticles Using Click Chemistry. Analytical Chemistry 84 (2012) 4267-4270 and Supporting information 15 pages.
Ensign et al. Photocatalytic Synthesis of Copper Colloids from Cu(II) by the Ferrihydrite Core of Ferritin. Inorganic Chemistry 43 (2004) 3441-3446 and Supporting Information 3 pages.
Drochioiu et al. Novel UV assay for protein determination and the characterization of copper-protein complexes by mass spectrometry. Talanta 69 (2006) 556-564.
File History of U.S. Appl. No. 14/734,678, filed Jun. 9, 2015.
File History of U.S. Appl. No. 15/674,831, filed Aug. 11, 2017.

QUANTITATIVE PEPTIDE OR PROTEIN ASSAY

CROSS-REFERENCE TO RELATED APPLICATIONS

This application is a divisional of U.S. patent application Ser. No. 15/674,831, filed Aug. 11, 2017, which is a divisional of Ser. No. 14/734,678, filed Jun. 9, 2015, which claims priority to U.S. Provisional Patent Application No. 62/010,594 filed Jun. 11, 2014, the entirety of which is incorporated by reference herein.

FIELD

Peptide and/or protein assay methods, compositions, and kits, useful for determining the concentration of small volume samples before analysis by mass spectrophotometry (MS) and other types of analyses.

BACKGROUND

Mass spectrometry (MS) is a sensitive method for the simultaneous identification and relative quantitation of thousands of proteins between multiple samples. On-going advancements in MS instrumentation continue to push the ability of the scientific community to characterize the protein dynamics in complex biological systems to a great depth. Despite MS capabilities, a majority of MS samples are analyzed without significant pre-injection characterization or normalization, because current methods to monitor and measure proteins, such as UV absorption or bichinconic acid (BCA) assays, work poorly with peptides, consume too much valuable sample, and lack the required sensitivity. This lack of sample characterization and normalization leads to difficulties with standardization and reproducibility of MS experiments and significant under-productive instrument time.

Commercially available colorimetric protein and peptide solution quantitation methods include biuret (Gornall et al. J. Biol. Chem. 177 (1949) 751), Lowry (Lowry et al. J. Biol. Chem. 193 (1951) 265), bicinchoninic acid (BCA) (Smith et al. Anal. Biochem. 150 (1985) 76), Coomassie Blue G-250 dye-binding (Bradford, Anal. Biochem. 72 (1976) 248), and colloidal gold (Stoscheck, Anal. Biochem. 160 (1987) 301).

The biuret method is based on a protein forming a complex with cupric ions. Peptide nitrogen binds to copper (II) ion under alkaline conditions, producing a purple color. The absorption maximum of the product is 550 nm. The sensitivity is 1 mg protein/ml to 6 mg protein/ml. The biuret method is a relatively insensitive protein determination method compared to other commercial methods of colorimetric protein determination.

Another method combines the biuret reaction and the copper(1)-bathocuproine chelate reaction (Determination of Proteins by a Reverse Biuret Method Combined with the Copper-Bathocuproine Chelate Reaction. *Clinica Chimica Acta.*, 216 (1993) 103-111). In this method, a sample protein forms a $Cu^{2+}$-protein chelate complex (biuret reaction) during the first step. Excess $Cu^{2+}$ is reduced to $Cu^+$ by ascorbic acid, allowing $Cu^+$ to form a $Cu^+$-bathocuproine chelate complex during the second step. The amount of $Cu^+$-bathocuproine chelate complex formed is inversely proportional to the protein concentration. This is a negative or indirect assay using a bathocuproine chelator to determine protein concentration.

The Lowry method is a modified biuret reaction. It occurs in two steps: first, peptide bonds react with copper(II) ions under alkaline conditions, then Folin-Ciocalteau phosphomolybdic-phosphotungstic acid reduces to heteropolymolybdenum blue by copper-catalyzed oxidation of aromatic amino acids. The absorption maximum of the product is 750 nm. The Lowry method is more sensitive than the biuret method, with a linear sensitivity of 0.1 mg protein/ml to 1.5 mg protein/ml for bovine serum albumin (BSA). Certain amino acids, detergents, lipids, sugars, and nucleic acids interfere with the reaction. The reaction is pH dependent and pH should be maintained between pH 10 and pH 10.5.

The BCA method is related to the Lowry method in that peptide bonds in proteins first reduce cupric ion ($Cu^{2+}$) to produce a tetradentate-cuprous ion ($Cu^{1+}$) complex in an alkaline medium. The cuprous ion complex then reacts with BCA (2 molecules BCA per $Cu^{1+}$) to form an intense purple color that can be measured at 562 nm. The BCA-Copper reaction is shown below:

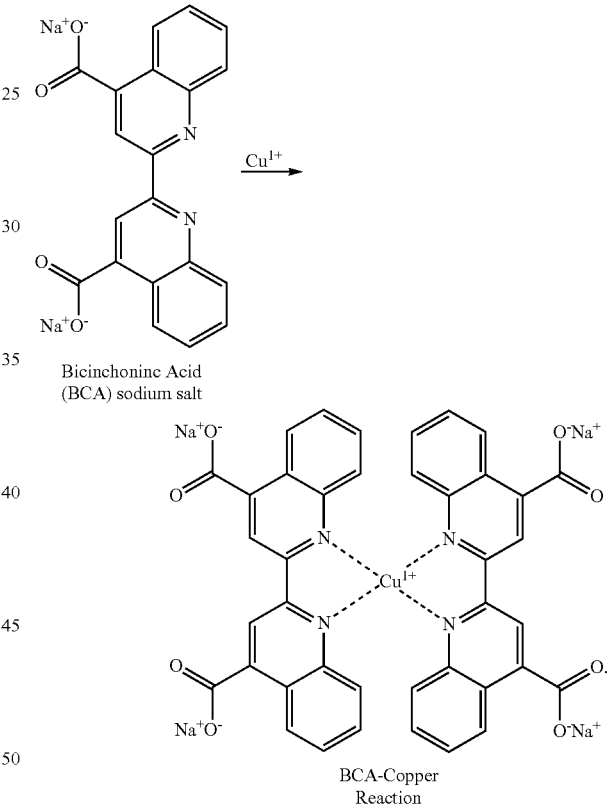

Bicinchoninic Acid (BCA) sodium salt

BCA-Copper Reaction

Because BCA is stable in alkaline medium, the BCA method can be carried out in one step, compared to two steps needed in the Lowry method. The BCA method better tolerates potential inhibitory or interfering compounds in the sample compared to the Lowry method. For example, up to 5% of each of sodium dodecyl sulfate (SDS), Triton X-100, and Tween-20 can be present and not interfere with the BCA method, compared to only 1% SDS, 0.03% Triton X-100, and 0.062% Tween-20 that can be present and not interfere with the Lowry method. The BCA method also has increased sensitivity and an expanded linear working range compared to the Lowry method.

A MICRO BOA™ Protein Assay Kit (Thermo Fisher Scientific) permits quantitation of dilute sample solutions (0.5 µg/ml to 20 µg/ml) by using larger sample volumes to obtain higher sensitivity. Despite the increased sensitivity, sample volume requirements limit or prevent its use for quantitation of many peptide samples.

A modified BCA assay to quantitate peptides (Kapoor et al. *Analytical Biochemistry*, 393 (2009) 138-140) acknowledges difficulties measuring peptide concentrations because of high interpeptide variation largely because of peptide hydrophobicity. The modified BCA method estimates peptide concentration by denaturing peptides by treatment at 95° C. for five minutes in the presence of SDS prior to incubation with the BCA working reagent. However, data below 500 µg/ml is very close to noise level and thus is not reliable.

U.S. Pat. No. 4,839,295 discloses using bicinchoninic acid as a chelator to detect proteins, measuring absorbance at 562 nm.

The colloidal gold method is the most sensitive among the colorimetric protein determination methods. Its sensitivity is about 2 µg/ml to 20 µg/ml protein. However, there is significant protein-to-protein variation. Protein binding to colloidal gold causes a shift in colloidal gold absorbance that is proportional to the amount of protein in solution. Most common reagents other than thiols and sodium dodecyl sulfate (SDS) are compatible with the colloidal gold method.

The Coomassie Blue G-250 dye-binding method is based on the immediate absorbance shift from 470 nm to 595 nm that occurs when Coomassie Blue G-250 binds protein in an acidic medium. Color development is rapid and the assay can be performed in ten minutes. The Coomassie Blue G-250 dye-binding method is comparatively free from interference by common reagents except detergents. There is moderate protein-to-protein variation and the method does not work well with peptides.

A total protein assay (Sozgen et al., Talanta, 68 (2006) 1601-1609 Spectrophotometric total protein assay with copper (II) neocuproine reagent in alkaline medium) uses copper(II)-neocuproine (Nc) reagent in alkaline medium with a hydroxide-carbonate-tartarate solution, with neocuproine as chelator. After 30 min incubation at 40° C., absorbance of the reduction product, Cu(I)-Nc complex, is read at 450 nm against a reagent blank. This assay has limited sensitivity because of the limited solubility of neocuproine in alkaline aqueous solution.

U.S. Pat. No. 5,693,291 discloses a quantitative protein method. The method is an indirect two-step method. It uses two reagents: reagent A (tartrate solution and copper sulfate) and reagent B (reducing agent, e.g., ascorbic acid, and bathocuproine chelator). Reagent A contains 0.7 to 2 mmol/l $Cu^{2+}$ ions and 2 to 4 mmol/l tartrate in alkaline solution. Reagent B contains 1 to 1.5 mmol/l ascorbic acid and 0.5 to 0.8 mmol/l bathocuproine. The proportion of reagent A to reagent B is 1:8 to 1:12, i.e., 1 part reagent A to 8-12 parts reagent B. The combined volume of reagent A and reagent B is between 750 µl and 3000 µl, which is relatively large. Step one of the method mixes 100 µl Reagent A to 50 µl sample, followed by incubating at room temperature for 5 min to 60 min. Step two of the method adds 1 ml reagent B to the step one mixture, followed by brief mixing and reading at 485 nm. This negative or indirect assay quantitates protein by the difference in absorbance in the pre- versus post-bathocuproine chelated sample. It is thus less accurate than a positive or direct assay that quantitates protein directly. It also uses a large volume of standard protein to reagent (volume standard protein to reagent A is 1:1.6 to 1:2.4).

The method provided herein overcomes such drawbacks and provides additional benefits.

SUMMARY

Figure 1:
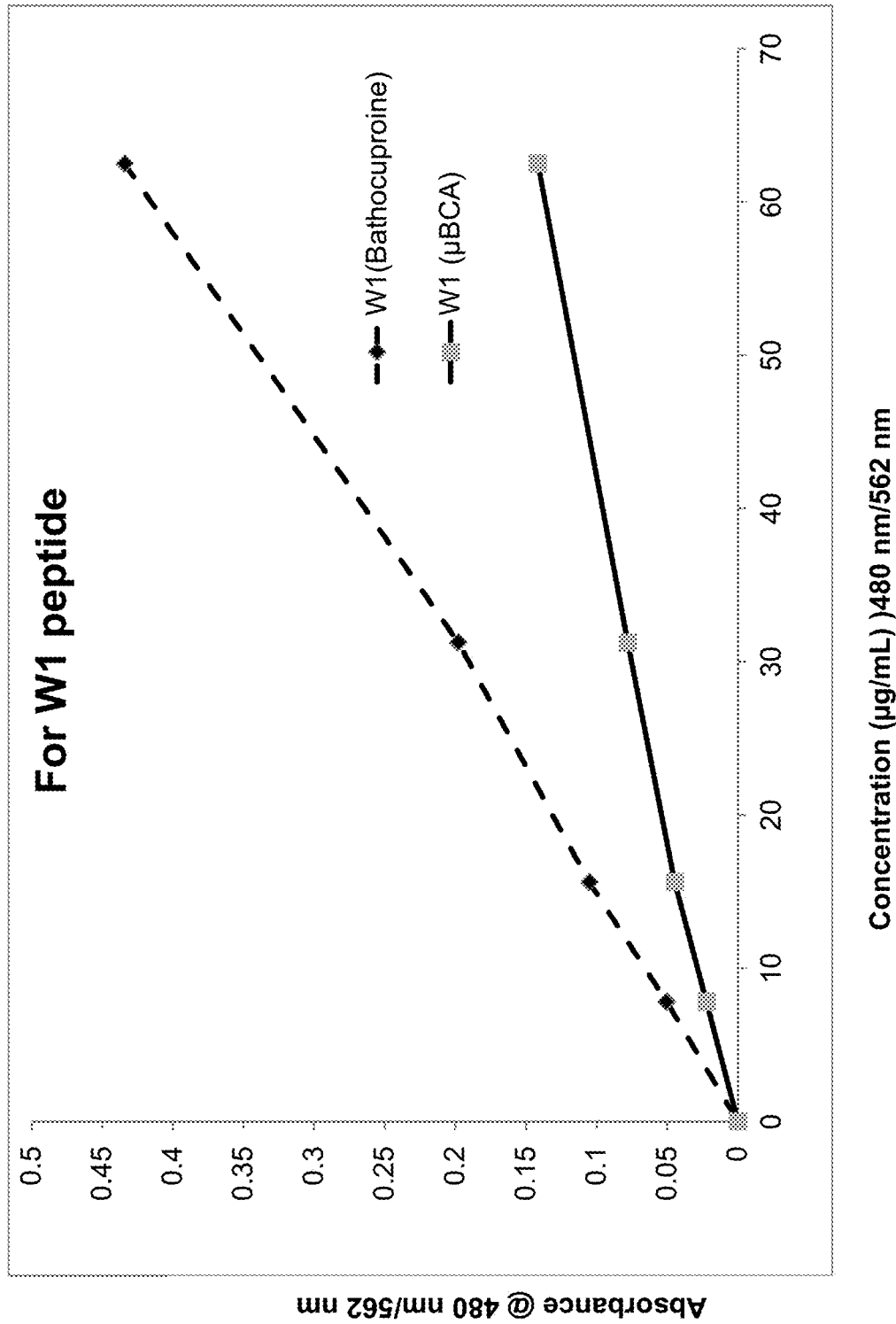
FIG. 1 shows peptide quantitation using a method according to certain embodiments provided herein compared to the commercial MICRO BCA™ method.

One non-limiting use of the methods provided herein is for MS quantitation of peptides or peptide mixtures. The methods according to the present disclosure use small sample volumes, and result in a robust signal with high signal to noise ratio (S/N) compared to other methods. The methods provided herein accurately quantitate complex peptide samples, such as those generated by tryptic digestion of proteins, cell lysates, plasma or serum samples, with low variability.

One embodiment provided herein is a direct method for determining peptide or protein concentration in a sample, the method comprising (a) combining the sample with a quantitation assay reagent composition comprising a complex to form a mixture where the complex comprises the following general formula:

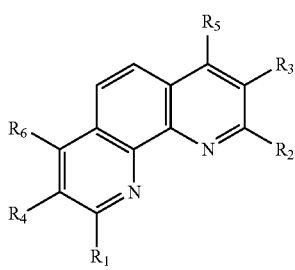

where each of $R_1$ and $R_2$ is independently alkyl including but not limited to a $C_1$-$C_6$ straight or branched alkyl or a $C_6$-$C_{20}$ aryl, alkylaryl, or arylalkyl such as methyl (—$CH_3$), ethyl (—$CH_2CH_3$), propyl (—$CH_2CH_2CH_3$), butyl (—$CH_2CH_2CH_2CH_3$) or phenyl (—$C_6H_5$);

each of $R_3$ and $R_4$ is independently selected from the group consisting of hydrogen (H), sulfonate (—$SO_3$—) salt of sodium ($Na^+$), potassium ($K^+$) or lithium ($Li^+$); phosphonate (—$PO_3$) salt of sodium ($Na^+$), potassium ($K^+$) or lithium ($Li^+$); and carboxylate (—$CO_2^-$) salt of sodium ($Na^+$), potassium ($K^+$) or lithium ($Li^+$); and each of $R_5$ and $R_6$ is

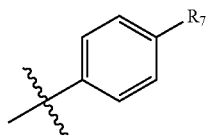

where $R_7$ is independently selected from the group consisting of hydrogen (H), sulfonate (—$SO_3$—) salt of sodium ($Na^+$), potassium ($K^+$) or lithium ($Li^+$); phosphonate (—$PO_3$—) salt of sodium ($Na^+$), potassium ($K^+$) or lithium ($Li^+$); and carboxylate (—$CO_2^-$) salt of sodium ($Na^+$), potassium ($K^+$) or lithium ($Li^+$);

with the proviso that at least one of $R_3$, $R_4$, and $R_7$ is not H;

(b) incubating the mixture under conditions sufficient to form a colored complex; and (c) measuring absorbance of the colored complex at 450 nm to 500 nm as a direct indicator of peptide or protein concentration in the sample.

The method may further comprise, after (c), determining the peptide or protein concentration in the sample by comparing the directly measured absorbance with the absorbance of at least one sample containing a known concentration of a standard. The sample may be a biological sample. The sample may be plasma or serum. The standard can be a peptide, a peptide mixture, or a protein digest. The method may be performed prior to mass spectrometry analysis of the sample. The reagent composition in (a) may further comprise tartrate and copper sulfate. The incubation temperature in (b) may range from room temperature to about 45° C., or from about 19° C. to about 22° C., or may be about 37° C., or may be about 45° C. The sample may be a plurality of peptides. The sample volume may be about 5 μl, may not exceed about 200 μl, may range from about 5 μl to about 20 μl, from about 10 μl to about 20 μl, or from about 15 μl to about 20 μl. Absorbance may be determined by an automated microplate reader. The standard may be a peptide, a peptide mixture, or a peptide digest at a known concentration. The sample may be in a solvent that is an aqueous solvent, an organic solvent, or an aqueous and organic solvent. The method may further comprise, after (c), analyzing the peptide(s) by mass spectrometry. An assay component may contain at least one of an organic solvent or a detergent to improve peptide or protein solubility. In one embodiment the reagent composition is bathocuproinedisulfonic acid disodium salt hydrate with about 50% acetonitrile. Absorbance may be read at about 480 nm.

Another embodiment provided herein is a direct method for determining peptide or protein concentration in a sample comprising:

(a) combining the sample with a quantitation assay reagent composition comprising a complex with 50% acetonitrile to form a mixture, where the complex comprises the following general formula:

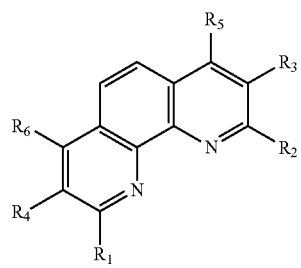

where each of $R_1$ and $R_2$ is independently alkyl including but not limited to a $C_1$-$C_6$ straight or branched alkyl or a $C_6$-$C_{20}$ aryl, alkylaryl, or arylalkyl such as methyl (—$CH_3$), ethyl (—$CH_2CH_3$), propyl (—$CH_2CH_2CH_3$), butyl (—$CH_2CH_2CH_2CH_3$) or phenyl (—$C_6H_5$);

each of $R_3$ and $R_4$ is independently selected from the group consisting of hydrogen (H), sulfonate (—$SO_3^-$) salt of sodium ($Na^+$), potassium ($K^+$) or lithium ($Li^+$); phosphonate (—$PO_3$) salt of sodium ($Na^+$), potassium ($K^+$) or lithium ($Li^+$); and carboxylate (—$CO_2^-$) salt of sodium ($Na^+$), potassium ($K^+$) or lithium ($Li^+$); and each of $R_5$ and $R_6$ is

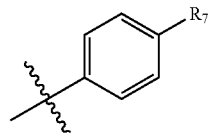

where $R_7$ is independently selected from the group consisting of hydrogen (H), sulfonate (—$SO_3^-$) salt of sodium ($Na^+$), potassium ($K^+$) or lithium ($Li^+$); phosphonate (—$PO_3$) salt of sodium ($Na^+$), potassium ($K^+$) or lithium ($Li^+$); and carboxylate (—$CO_2^-$) salt of sodium ($Na^+$), potassium ($K^+$) or lithium ($Li^+$);

with the proviso that at least one of $R_3$, $R_4$, and $R_7$ is not H;

(b) incubating the mixture under conditions sufficient to form a colored complex; and (c) measuring absorbance of the colored complex at 450 nm to 500 nm as a direct indicator of peptide or protein concentration in the sample.

The method may further comprise, after (c), determining the peptide or protein concentration in the sample by comparing the directly measured absorbance with the absorbance of at least one sample containing a known concentration of a standard. The standard may be a peptide, a peptide mixture, or a protein digest. The method may be performed prior to mass spectrometry analysis of the sample.

The reagent composition in (a) may further comprises tartrate and copper sulfate. The incubation temperature in (b) may range from room temperature to about 45° C. or from about 19° C. to about 22° C., or may be about 37° C., or may be about 45° C. The sample volume may range from about 5 µl to about 20 µl. The sample may be a plurality of peptides. The sample volume may be about 5 µl, or may range from about 10 µl to about 20 µl, or from about 15 µl to about 20 µl, or may not exceed about 200 µl. Absorbance may be determined by an automated microplate reader. The standard may be a peptide, a peptide mixture, or a peptide digest at a known concentration. In the method, after (c), the peptide(s) may be analyzed by mass spectrometry. In one embodiment, the reagent composition is bathocuproinedisulfonic acid disodium salt hydrate. Absorbance may be read at about 480 nm. The sample may be a biological sample. The sample may be serum or plasma sample.

Another embodiment provided herein is a peptide quantitation reagent composition comprising at least one excipient and (a) a complex at a concentration ranging from about 0.04 M to about 0.1 M where the complex comprises the following general formula:

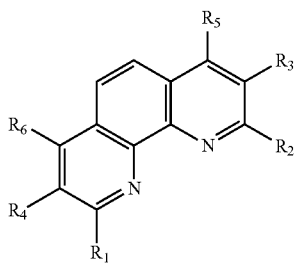

where
each of R1 and R2 is independently alkyl including but not limited to a $C_1$-$C_6$ straight or branched alkyl or each of $R_1$ and $R_2$ is independently alkyl including but not limited to a $C_1$-$C_6$ straight or branched alkyl or a $C_6$-$C_{20}$ aryl, alkylaryl, or arylalkyl such as methyl (—$CH_3$), ethyl (—$CH_2CH_3$), propyl (—$CH_2CH_2CH_3$), butyl (—$CH_2CH_2CH_2CH_3$) or phenyl (—$C_6H_5$);

each of $R_3$ and $R_4$ is independently selected from the group consisting of hydrogen (H), sulfonate (—$SO_3^-$) salt of sodium ($Na^+$), potassium ($K^+$) or lithium ($Li^+$); phosphonate (—$PO_3$) salt of sodium ($Na^+$), potassium ($K^+$) or lithium ($Li^+$); and carboxylate (—$CO_2^-$) salt of sodium ($Na^+$), potassium ($K^+$) or lithium ($Li^+$); and each of $R_5$ and $R_6$ is

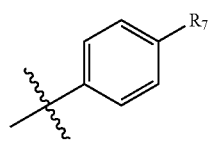

where $R_7$ is independently selected from the group consisting of hydrogen (H), sulfonate (—$SO_3$) salt of sodium ($Na^+$), potassium ($K^+$) or lithium ($Li^+$); phosphonate (—$PO_3$) salt of sodium ($Na^+$), potassium ($K^+$) or lithium ($Li^+$); and carboxylate (—$CO_2^-$) salt of sodium ($Na^+$), potassium ($K^+$) or lithium ($Li^+$);

with the proviso that at least one of $R_3$, $R_4$, and $R_7$ is not H;

(b) tartrate at a concentration ranging from about 5.7 mM to about 22.7 mM, and (c) copper sulfate at a concentration ranging from about 0.25 mM to about 0.5 mM, resulting in a peptide quantitation reagent composition.

Another embodiment provided herein is a peptide quantitation reagent composition comprising at least one excipient and (a) a complex at a concentration ranging from about 0.04 M to about 0.1 M in 50% acetonitrile, where the complex comprises the following general formula:

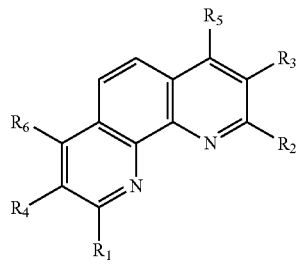

where
each of $R_1$ and $R_2$ is independently alkyl including but not limited to a $C_1$-$C_6$ straight or branched alkyl or a $C_6$-$C_{20}$ aryl, alkylaryl, or arylalkyl such as methyl (—$CH_3$), ethyl (—$CH_2CH_3$), propyl (—$CH_2CH_2CH_3$), butyl (—$CH_2CH_2CH_2CH_3$) or phenyl (—$C_6H_5$);

each of $R_3$ and $R_4$ is independently selected from the group consisting of hydrogen (H), sulfonate (—$SO_3^-$) salt of sodium ($Na^+$), potassium ($K^+$) or lithium ($Li^+$); phosphonate (—$PO_3$) salt of sodium ($Na^+$), potassium ($K^+$) or lithium ($Li^+$); and carboxylate (—$CO_2^-$) salt of sodium ($Na^+$), potassium ($K^+$) or lithium ($Li^+$); and each of $R_5$ and $R_6$ is

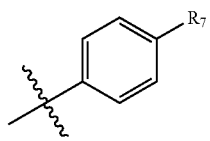

where $R_7$ is independently selected from the group consisting of hydrogen (H), sulfonate (—$SO_3^-$) salt of sodium ($Na^+$), potassium ($K^+$) or lithium ($Li^+$); phosphonate (—$PO_3$) salt of sodium ($Na^+$), potassium ($K^+$) or lithium ($Li^+$); and carboxylate (—$CO_2^-$) salt of sodium ($Na^+$), potassium ($K^+$) or lithium ($Li^+$);

with the proviso that at least one of $R_3$, $R_4$, and $R_7$ is not H;

(b) tartrate at a concentration ranging from about 5.7 mM to about 22.7 mM, and (c) copper sulfate at a concentration ranging from about 0.25 mM to about 0.5 mM, resulting in a peptide quantitation reagent composition.

Another embodiment provided herein is a peptide quantitation reagent kit comprising instructions for mass spectroscopy quantitation of peptides using the kit, and reagents comprising (a) a complex comprising the following general formula:

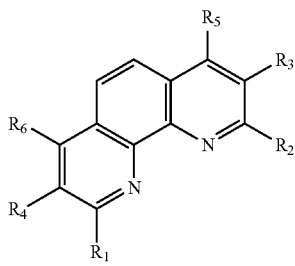

where each of $R_1$ and $R_2$ is independently alkyl including but not limited to a $C_1$-$C_6$ straight or branched alkyl or a $C_6$-$C_{20}$ aryl, alkylaryl, or arylalkyl such as methyl (—$CH_3$), ethyl (—$CH_2CH_3$), propyl (—$CH_2CH_2CH_3$), butyl (—$CH_2CH_2CH_2CH_3$) or phenyl (—$C_6H_5$);

each of $R_3$ and $R_4$ is independently selected from the group consisting of hydrogen (H), sulfonate (—$SO_3^-$) salt of sodium ($Na^+$), potassium ($K^+$) or lithium ($Li^+$); phosphonate (—$PO_3$) salt of sodium ($Na^+$), potassium ($K^+$) or lithium ($Li^+$); and carboxylate (—$CO_2^-$) salt of sodium ($Na^+$), potassium ($K^+$) or lithium ($Li^+$); and each of $R_5$ and $R_6$ is

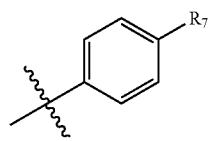

where $R_7$ is independently selected from the group consisting of hydrogen (H), sulfonate (—$SO_3^-$) salt of sodium ($Na^+$), potassium ($K^+$) or lithium ($Li^+$); phosphonate (—$PO_3$) salt of sodium ($Na^+$), potassium ($K^+$) or lithium ($Li^+$); and carboxylate (—$CO_2^-$) salt of sodium ($Na^+$), potassium ($K^+$) or lithium ($Li^+$);

with the proviso that at least one of $R_3$, $R_4$, and $R_7$ is not H;

(b) tartrate, and (c) copper sulfate, the composition having pH ranging from about pH 12 to about pH 13.

Another embodiment provided herein is a peptide quantitation reagent kit comprising instructions for mass spectroscopy quantitation of peptides using the kit, and reagents comprising (a) a complex in 50% acetonitrile, where the complex contains the following general formula:

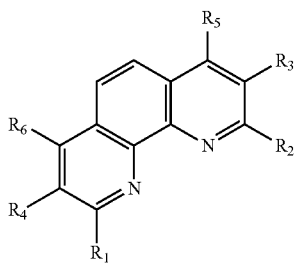

where each of $R_1$ and $R_2$ is independently alkyl including but not limited to a $C_1$-$C_6$ straight or branched alkyl or a $C_6$-$C_{20}$ aryl, alkylaryl, or arylalkyl such as methyl (—$CH_3$), ethyl (—$CH_2CH_3$), propyl (—$CH_2CH_2CH_3$), butyl (—$CH_2CH_2CH_2CH_3$) or phenyl (—$C_6H_5$);

each of $R_3$ and $R_4$ is independently selected from the group consisting of hydrogen (H), sulfonate (—$SO_3^-$) salt of sodium ($Na^+$), potassium ($K^+$) or lithium ($Li^+$); phosphonate (—$PO_3$) salt of sodium ($Na^+$), potassium ($K^+$) or lithium ($Li^+$); and carboxylate (—$CO_2^-$) salt of sodium ($Na^+$), potassium ($K^+$) or lithium ($Li^+$); and each of $R_5$ and $R_6$ is

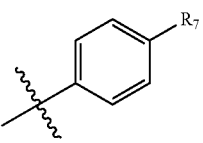

where $R_7$ is independently selected from the group consisting of hydrogen (H), sulfonate (—$SO_3^-$) salt of sodium ($Na^+$), potassium ($K^+$) or lithium ($Li^+$); phosphonate (—$PO_3$) salt of sodium ($Na^+$), potassium ($K^+$) or lithium ($Li^+$); and carboxylate (—$CO_2^-$) salt of sodium ($Na^+$), potassium ($K^+$) or lithium ($Li^+$);

with the proviso that at least one of $R_3$, $R_4$, and $R_7$ is not H;

(b) tartrate, and (c) copper sulfate, the composition having pH ranging from about pH 12 to about pH 13.

Another embodiment provided herein is a direct method for determining peptide or protein concentration in a sample, the method comprising:

(a) combining the sample with a quantitation assay reagent composition comprising a complex to form a mixture where the complex is

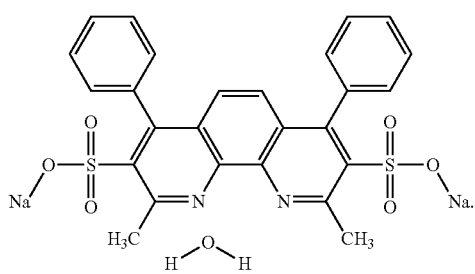

(b) incubating the mixture under conditions sufficient to form a colored complex; and (c) measuring absorbance of the colored complex at 450 nm to 500 nm as a direct indicator of peptide or protein concentration in the sample.

The method may further comprise, after (c), determining the peptide or protein concentration in the sample by comparing the directly measured absorbance with the absorbance of at least one sample containing a known concentration of a standard. The sample may be a biological sample. The sample may be plasma or serum. The standard can be a peptide, a peptide mixture, or a protein digest. The method may be performed prior to mass spectrometry analysis of the sample. The reagent composition in (a) may further comprises tartrate and copper sulfate. The incubation temperature in (b) may range from room temperature to about 45° C., or from about 19° C. to about 22° C., or may be about 37° C., or may be about 45° C. The sample may be a plurality of peptides. The sample volume may be about 5 µl, may not exceed about 200 µl, may range from about 5 µl to about 20 µl, from about 10 µl to about 20 µl, or from about 15 µl to about 20 µl. Absorbance may be determined by an automated microplate reader. The standard may be a peptide, a peptide mixture, or a peptide digest at a known concentration. The sample may be in a solvent that is an aqueous solvent, an organic solvent, or an aqueous and organic solvent. The method may further comprise, after (c), analyzing the peptide(s) by mass spectrometry. An assay component may contain at least one of an organic solvent or a detergent to improve peptide or protein solubility. In one embodiment the reagent composition is bathocuproinedisulfonic acid disodium salt hydrate with about 50% acetonitrile. Absorbance may be read at about 480 nm.

Another embodiment provided herein is a direct method for determining peptide or protein concentration in a sample comprising:

(a) combining the sample with a quantitation assay reagent composition comprising a complex with 50% acetonitrile to form a mixture, where the complex contains

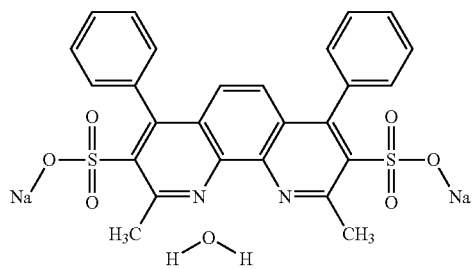

(b) incubating the mixture under conditions sufficient to form a colored complex; and (c) measuring absorbance of the colored complex at 450 nm to 500 nm as a direct indicator of peptide or protein concentration in the sample.

The method may further comprise, after (c), determining the peptide or protein concentration in the sample by comparing the directly measured absorbance with the absorbance of at least one sample containing a known concentration of a standard. The standard may be a peptide, a peptide mixture, or a protein digest. The method may be performed prior to mass spectrometry analysis of the sample. The reagent composition in (a) may further comprises tartrate and copper sulfate. The incubation temperature in (b) may range from room temperature to about 45° C. or from about 19° C. to about 22° C., or may be about 37° C., or may be about 45° C. The sample volume may range from about 5 µl to about 20 µl. The sample may be a plurality of peptides. The sample volume may be about 5 µl, or may range from about 10 µl to about 20 µl, or from about 15 µl to about 20 µl, or may not exceed about 200 µl. Absorbance may be determined by an automated microplate reader. The standard may be a peptide, a peptide mixture, or a peptide digest at a known concentration. In the method, after (c), the peptide(s) may be analyzed by mass spectrometry. In one embodiment, the reagent composition is bathocuproinedisulfonic acid disodium salt hydrate. Absorbance may be read at about 480 nm. The sample may be a biological sample. The sample may be serum or plasma sample.

Another embodiment provided herein is a peptide quantitation reagent composition comprising at least one excipient and (a) a complex at a concentration ranging from about 0.04 M to about 0.1 M where the complex contains

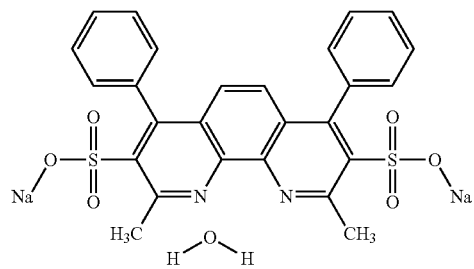

(b) tartrate at a concentration ranging from about 5.7 mM to about 22.7 mM, and (c) copper sulfate at a concentration ranging from about 0.25 mM to about 0.5 mM, resulting in a peptide quantitation reagent composition.

Another embodiment provided herein is a peptide quantitation reagent composition comprising at least one excipient and (a) a complex at a concentration ranging from about 0.04 M to about 0.1 M in 50% acetonitrile, where the complex contains

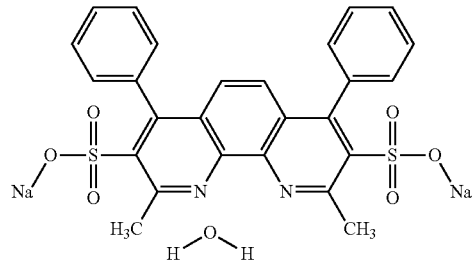

(b) tartrate at a concentration ranging from about 5.7 mM to about 22.7 mM, and (c) copper sulfate at a concentration ranging from about 0.25 mM to about 0.5 mM, resulting in a peptide quantitation reagent composition.

Another embodiment provided herein is a peptide quantitation reagent kit comprising instructions for mass spectroscopy quantitation of peptides using the kit, and reagents comprising (a) a complex containing

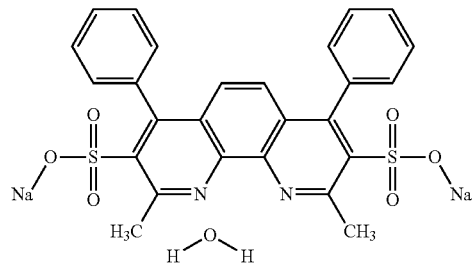

(b) tartrate, and (c) copper sulfate, the composition having pH ranging from about pH 12 to about pH 13.

Another embodiment provided herein is a peptide quantitation reagent kit comprising instructions for mass spectroscopy quantitation of peptides using the kit, and reagents comprising (a) a complex in 50% acetonitrile, where the complex contains

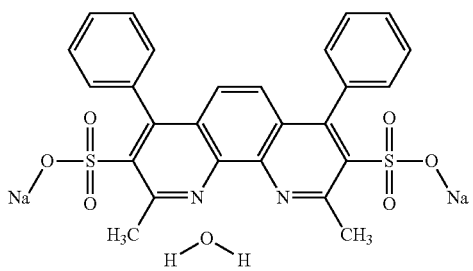

(b) tartrate, and (c) copper sulfate, the composition having pH ranging from about pH 12 to about pH 13.

These and other embodiments will be further described as follows.

DETAILED DESCRIPTION

Bathocuproinedisulfonic acid disodium salt hydrate has 500% greater solubility in water compared to bathocuproine or neocuprione. The increased solubility allows higher concentrations of chelator in solution which ultimately provides better sensitivity.

The methods described herein provide increased sensitivity of peptide concentration determination. In one embodiment, sensitivity was as low as ok 25 µg/ml. In one embodiment, sensitivity was as low as 15 µg/ml peptide. In one embodiment, sensitivity ranged from 12.5 µg/ml-1000 µg/ml. The methods provided herein do not require peptide denaturation prior to performing the assay. Peptide denaturation on very small sample volumes is highly variable and time consuming. Eliminating the need for denaturation results in shorter assay duration and less assay variability.

The methods according to the present disclosure are positive or direct assays. They require a volume of about 200 µl, comprised of a sample volume from 10 µl to 20 µl, and a reagent volume of 180 µl. The methods provided herein allow higher levels of sensitivity to be achieved at a smaller sample volume compared to other commercial assays. The smaller volume enables the methods provided herein to be performed in a multi-well plate and to be read by an automatic reader, versus reading in cuvettes that typically require several, 0.5 ml to 2 mls of sample. The methods described herein permit use of much smaller sample volumes and smaller total volumes compared with the MICRO BCA™ method. The MICRO BCA™ assay requires 150 µl sample volume and 300 µl total volume. The previously described "negative" bathocuproine assay requires 50 µl sample volume and 1.15 ml total volume. In favorable contrast, the methods according to the present disclosure require 20 µl maximum sample volume and 200 µl total volume.

Like other copper based protein assays, certain amino acids in a peptide can increase or decrease the sensitivity of the methods. Peptide solubility and structure can also have an influence on the results. The methods provided herein are best used to quantitate peptides in complex samples containing a mixture of peptides where differences in peptide length and sequence are averaged out in the assay. This is of particular importance in measuring recovery from peptide fractionation methods or standardizing HPLC load amounts for quantitative proteomic analysis. The methods disclosed herein can also be used to assay samples containing a single peptide, however, this can result in increased error, resulting from a larger variation in assay response among different peptides compared to a standard. This can be compensated for by using standards more specific to the peptide of interest.

The methods provided herein are one-step (mix and read), and absorbance is read at 450 nm to 500 nm, in one embodiment at 480 nm.

The methods described herein provide for multiple peptide assays that allow detection and quantification of complex peptide mixtures before standard MS analysis in about 30 minutes.

The methods described herein provide 2-3 fold enhanced signal to background ratio (S/B) than the MICRO BCA™ assay at same sample volumes.

The methods provided herein exhibit decreased peptide to peptide variability due to solubilizing hydrophobic peptides by adding an organic co-solvent such as acetonitrile, detergents such as SDS and urea, and other water miscible organic solvents.

In certain embodiments, the peptide quantitation methods provided herein use a compound as chelator having the following general formula

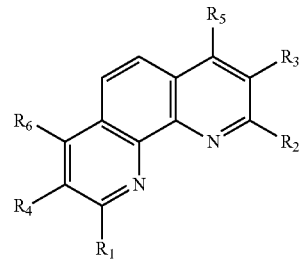

where each of $R_1$ and $R_2$ is independently alkyl including but not limited to a $C_1$-$C_6$ straight or branched alkyl or a $C_6$-$C_{20}$ aryl, alkylaryl, or arylalkyl such as methyl (—$CH_3$), ethyl (—$CH_2CH_3$), propyl (—$CH_2CH_2CH_3$), butyl (—$CH_2CH_2CH_2CH_3$) or phenyl (—$C_6H_5$);

each of $R_3$ and $R_4$ is independently selected from the group consisting of hydrogen (H), sulfonate (—$SO_3^-$) salt of sodium ($Na^+$), potassium ($K^+$) or lithium ($Li^+$); phosphonate (—$PO_3$) salt of sodium ($Na^+$), potassium ($K^+$) or lithium ($Li^+$); and carboxylate (—$CO_2^-$) salt of sodium ($Na^+$), potassium ($K^+$) or lithium ($Li^+$);

each of $R_5$ and $R_6$ is

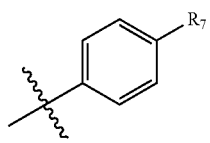

where $R_7$ is independently selected from the group consisting of hydrogen (H), sulfonate ($-SO_3^-$) salt of sodium ($Na^+$), potassium ($K^+$) or lithium ($Li^+$); phosphonate ($-PO_3$) salt of sodium ($Na^+$), potassium ($K^+$) or lithium ($Li^+$); and carboxylate ($-CO_2^-$) salt of sodium ($Na^+$), potassium ($K^+$) or lithium ($Li^+$);

with the proviso that at least one of $R_3$, $R_4$, and $R_7$ is not H.

In one embodiment, the peptide quantitation methods provided herein use as chelator bathocuproinedisulfonic acid disodium salt hydrate shown below:

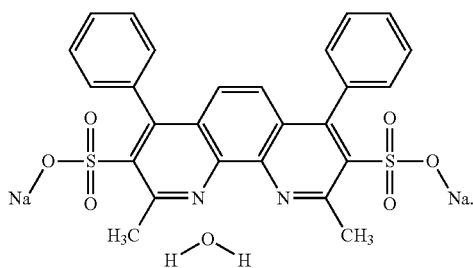

Without being held to a single theory, the complex increases the solubility of the bathocuproine, resulting in enhanced performance in the methods provided herein compared to previous methods.

The methods provided herein contain a higher amount of $Cu^{+2}$ (80 mg/ml). The methods provided herein reduce $Cu^{+2}$ to $Cu^+$ as in the BCA method, but in the instant methods the bathocuproine ion then combines with $Cu^+$ forming a green/orange complex with an absorbance in the range of 450 nm to 500 nm, in one embodiment at 480 nm.

The absorbance-based methods according to certain embodiments provided herein were evaluated with different peptides and protein digests. Assay conditions such as peptide concentration, detection reagent concentration, pH, incubation time, temperature and the ratio of different components were optimized. The peptides were assayed on a multi-well plate (e.g., 96 well plate) and the measurements were conducted using a spectrophotometer to measure absorbance at 480 nm.

EXAMPLE

In one embodiment, 20 μl sample is added to a prepared or pre-made working reagent (which is made by mixing 6.9 mM sodium tartrate dihydrate, 0.04 M bathocuproinedisulfonic acid disodium salt, and 0.32 M copper sulfate). The solution is mixed for one minute, incubated for 30 minutes at 37° C. and absorbance is measured at 480 nm.

A working solution is prepared by combining three solutions. Solution 1 is prepared by mixing sodium tartrate, sodium carbonate, sodium hydroxide, and sodium bicarbonate into water. Solution 2 is prepared by mixing bathocuproinedisulfonic acid, disodium salt hydrate into water optionally containing acetonitrile. Solution 3 is prepared by mixing cupric sulfate pentahydrate into water. The working solution is formed by combining solutions 1, 2, and 3. Specifically, solution 1 is prepared by mixing, into 50 ml water, 80 mg sodium tartrate (6.9 mM), 3.42 g sodium carbonate (0.65 M), 0.525 ml sodium hydroxide, and 0.89 g sodium bicarbonate (0.22 M). Solution 2 is prepared by mixing, into 50 ml 50% acetonitrile (25 ml acetonitrile, 25 ml water), 1.13 g bathocuproinedisulfonic acid disodium salt hydrate (0.04 M). Solution 3 is prepared by mixing, into 2 ml water, 160 mg cupric sulfate pentahydrate (0.32 M).

The working solution is formed by combining 50 parts Solution 1, 48 parts Solution 2, and 2 parts Solution 3.

A volume of 5 μl to 20 μl, typically 20 μl, of standard or sample containing peptides or protein is combined with the working solution, shaken for one minute, and incubated from about 22° C. to about 45° C. for, preferably 37° C., for 30 minutes. In one embodiment, 20 μl standard or sample is combined with 180 μl working solution, shaken for one min, and incubated at 45° C. for 30 minutes. In one embodiment, incubation is at 37° C. After incubation, absorbance at 480 nm is measured. The pH range of the final assay mixture is about pH 12 to 13.

While automated absorbance readings, using automated plate readers, are desirable for speed and convenience, the absorbance measurement of the reaction mixture measured in a cuvette may still be used.

In one embodiment, the methods provided herein quantitate peptides to be subjected to MS analysis. Peptides may include mass tags such as TMT or other covalent modifications used in MS. Peptides to be quantitated may include one or more heavy isotope labeled amino acids.

In one embodiment, the methods provided herein use single peptide or digested protein standard to generate a standard curve for peptide and/or protein quantitation. In another embodiment, a protein standard is used to generate a standard curve for protein quantitation. The accuracy and precision by which a standard curve is generated is crucial for accurate and precise sample measurement. In one embodiment, a standard curve comprises a mixture of peptides generated from a tryptic digest of bovine serum albumin (BSA) or Protein A/G using methods known in the art. Choice of a standard that produces an assay response close to the average for the sample type being analyzed produces the most accurate results.

Another embodiment provides for kits containing reagents and instructions for performing the methods described herein. For example, the kit may contain some or all of the reagents, and instructions, needed to prepare the working solution; one or more standards or instructions to prepare the standards; instructions to perform the assay; microwell plates, etc.

Over 30 different peptides, peptide mixtures, digests, and samples consistent with standard MS analysis were evaluated and are, summarized in Table 1. A majority (over 70%) of the samples showed reproducible and linear results.

TABLE 1

| Peptide | Sequence | MW (Da) | Ref. # | SEQ ID NO |
|---|---|---|---|---|
| w/o Lysine | | | | |
| VIP (1-12), human, porcine, rat | HSDAVFTDNYTR | 1425.5 | W1 | 1 |
| Beta-Amyloid (1-12) | DAEFRHDSGYEV | 1424.5 | W2 | 2 |
| Beta-Amyloid (1-8)-Cys | DAEFRHDSC | 1079.1 | W3 | 3 |
| Beta-Amyloid (1-13) | DAEFRHDSGYEVH | 1561.6 | W4 | 4 |

TABLE 1-continued

| Peptide | Sequence | MW (Da) | Ref. # | SEQ ID NO |
|---|---|---|---|---|
| mid-Lysine | | | | |
| Amyloid Precursor Protein (APP) (667-676) | SEVKMDAEFR | 1211.4 | M1 | 5 |
| ACTH (1-17) | SYSMEHFRWGKPVGKKR | 2093.4 | M2 | 6 |
| Beta-Amyloid (4-17) | FRHDSGYEVHHQKL | 1752.9 | M3 | 7 |
| Histatin-8 [Hemagglutination-Inhibiting Peptide (HIP)] | KFHEKHHSHRGY | 1562.7 | M4 | 8 |
| C-terminus Lysine | | | | |
| VSV-G Peptide | YTDIEMNRLGK | 1339.5 | E1 | 9 |
| Beta-Amyloid (3-16) | EFRHDSGYEVHHQK | 1768.9 | E2 | 10 |
| Beta-Amyloid (1-16) | DAEFRHDSGYEVHHQK | 1955 | E3 | 11 |
| Antennapedia Peptide, acid | RQIKIWFQNRRMKWKK | 2246.8 | E4 | 12 |
| CEF26, Influenza VirusNP (265-274) | ILRGSVAHK | 980.2 | E5 | 13 |
| MOG (35-55), mouse, rat | MEVGWYRSPFSRWHLYRNGK | 2582 | E6 | 14 |
| w/o Lysine | | | | |
| ACTH (1-10) | SYSMEHFRWG | 1299.4 | W5 | 15 |
| [Ile-Ser]-Bradykinin (T-Kinin) | ISRPPGFSPFR | 1260.5 | W6 | 16 |
| Leptin (93-105), human | NVIQISNDLENLR | 1527.7 | W7 | 17 |
| mid-Lysine | | | | |
| Beta-Amyloid (10-20) | YEVHHQKLVFF | 1446.7 | M5 | 18 |
| [Lys8,9]-Neurotensin (8-13) | KKPYIL | 761 | M6 | 19 |
| OVA (257-264) | SIINFEKL | 963.2 | M7 | 20 |
| c-terminus Lysine | | | | |
| Dynorphin A (2-13), porcine | GGFLRRIRPKLK | 1440.8 | E7 | 21 |
| Beta-Amyloid (18-28) | VFFAEDVGSNK | 1212.3 | E8 | 22 |

Figure 2:
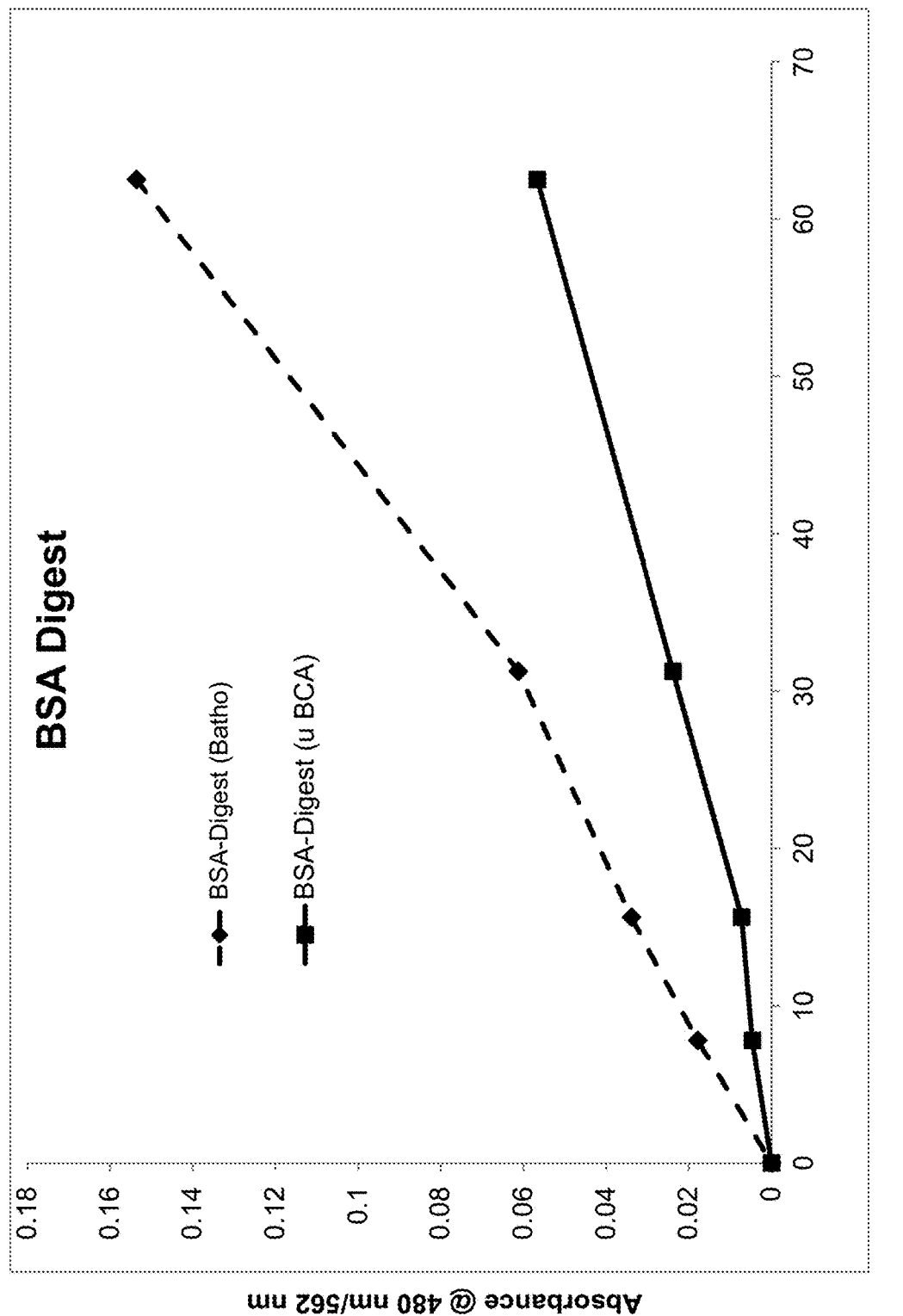
FIG. 2 shows a digest quantitation using a method according to certain embodiments provided herein compared to the commercial MICRO BCA™ method.
Figure 3:
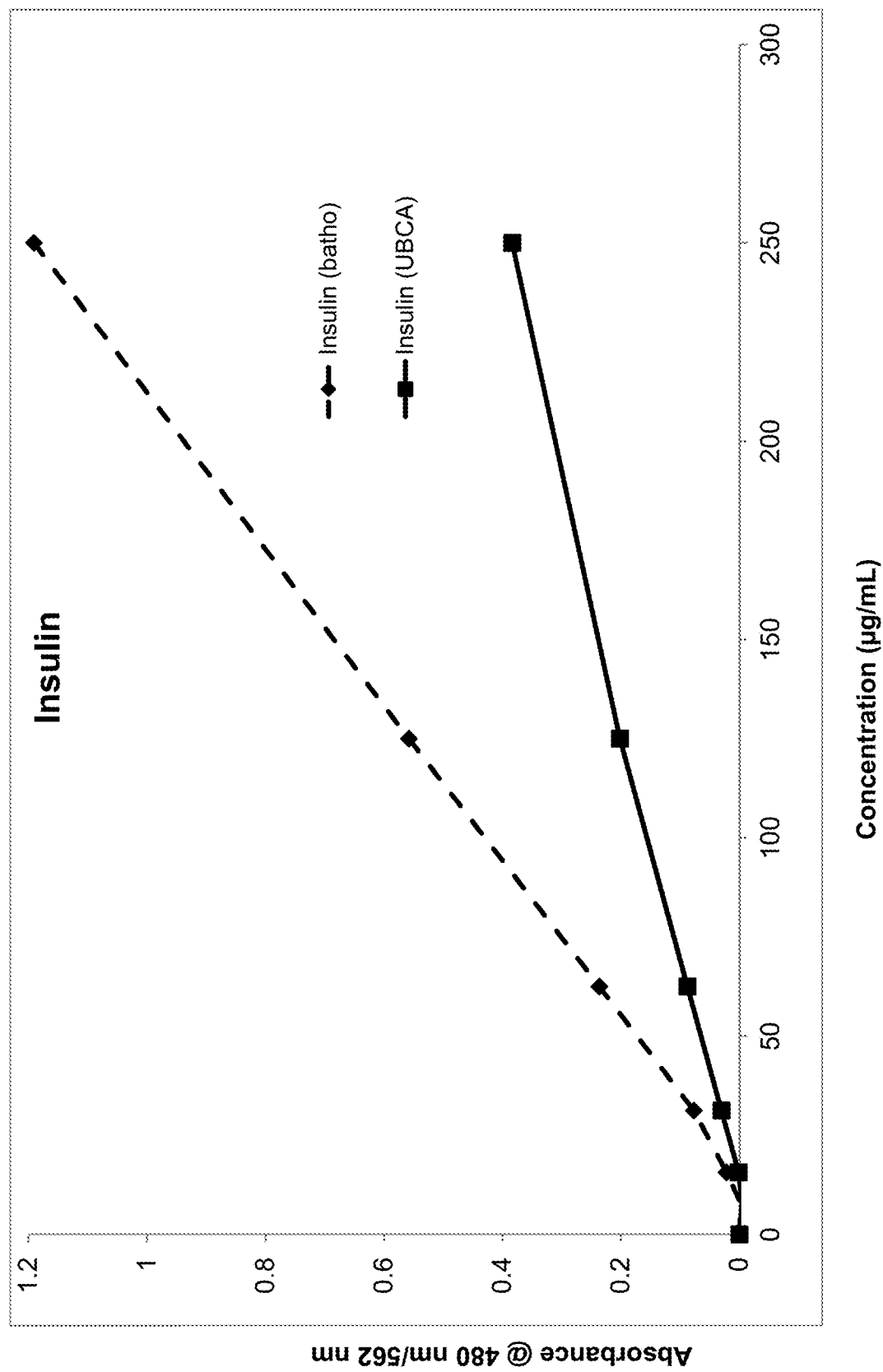
FIG. 3 shows another peptide quantitation using a method according to certain embodiments provided herein compared to the commercial MICRO BCA™ method.

The methods described herein using bathocuproinedisulfonic acid disodium salt hydrate method are sensitive down to 25 µg/ml peptide. This sensitivity substantially exceeds that of the MICRO BCA™ assay, which is more sensitive than the standard BCA method. Sensitivity is shown in FIGS. 1-3 quantitating peptide W1 (FIG. 1), BSA digest (FIG. 2) and insulin (FIG. 3), respectively. Limit of quantitation (LOQ) was calculated using the equation (10×(st. dev. of blank+avg. of blank)) and the LOQ for the method described herein and the MICRO BCA™ assay was 21.58 µg/ml and 77.40 µg/ml respectively.

Standard solution, peptide samples, or protein digests were loaded at 20 µl/well into microplates. Assay working reagent was added at 180 µl/well working solution. The plate was sealed, quickly mixed and incubated for 30 minutes at 22° C.-45° C. Absorbance was read at 480 nm using a SPECTRAMAX™ Plus384 or VARIOSKAN™ Flash (Type 3001) microplate reader. The established working peptide concentration range for the absorbance assays was 25 µg/ml-1000 µg/ml. Sample volumes of 5 µl-20 µl were used allowing for <1 µg peptide to be loaded for an assay sample for the absorbance assay.

The method described herein demonstrated 3-4 fold increase in S/N, compared to the MICRO BCA™ assay for all peptides tested. The average concentration at the limit of quantification (LOQ) was about 15 µg/ml.

The method described herein provides a robust signal and thus results in improved signal/background (S/B) ratio, which is the ratio of absorbance at 480 nm at a particular concentration to the absorbance at 480 nm of a blank. This is obtained, e.g., by the following calculation:

$$\text{Signal/Background }(S/B)\text{ at 500 µg/mL} = \frac{A_{480} \text{ of 500 µg/mL sample}}{A_{480} \text{ of blank}}$$

As shown in FIG. 1 for peptide W1, the present method yielded S/B of 311, compared to the MICRO BCA™ assay S/B of 87. Similarly, as shown in FIG. 2 for BSA digest, the present method yielded S/B of 201 compared to the MICRO BCA™ assay S/B of 55. For insulin (FIG. 3), the present method yielded S/B of 269 compared to the MICRO BCA™ assay S/B of 81. The present method showed a 3-4 fold increase in signal over the MICRO BCA™ assay. These peptides differed in peptide length and hydrophobicity which resulted in different sensitivity; Table 1 provides exact sequences.

Figure 4:
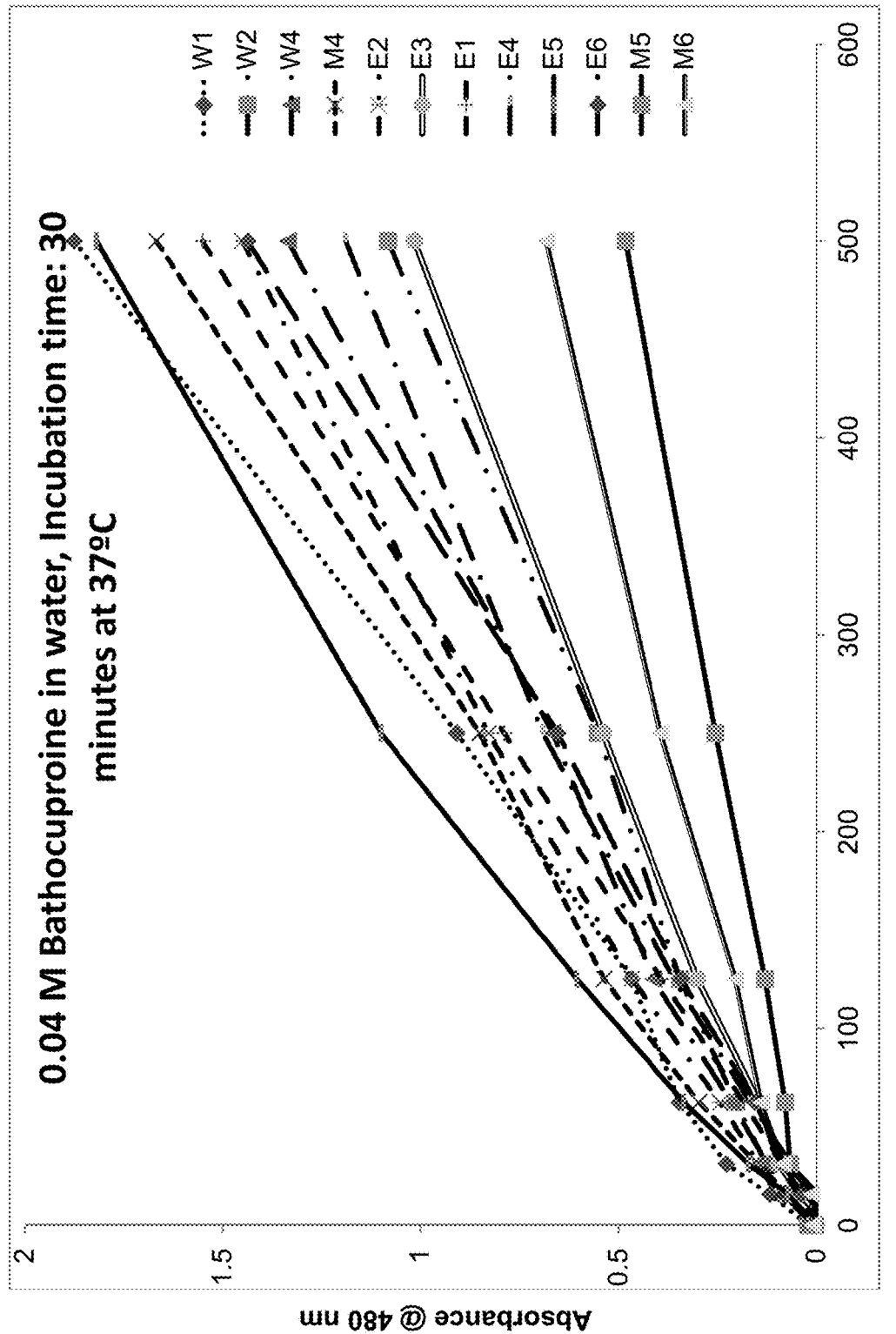
FIG. 4 shows peptide quantitation and variability using an embodiment of the methods provided herein.
Figure 5A:
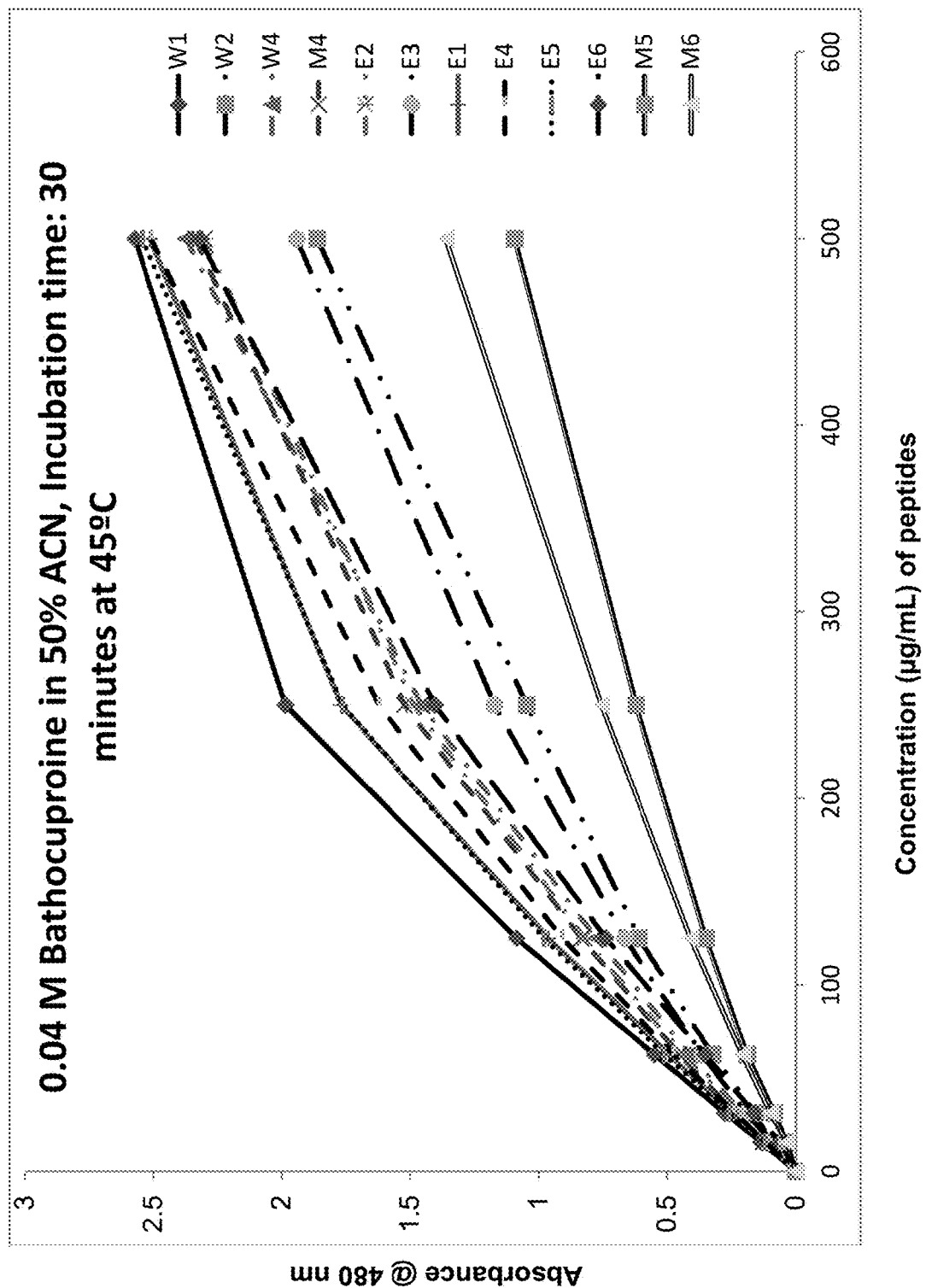
FIGS. 5A-B show peptide quantitation and variability using other embodiments of the methods provided herein.
Figure 5B:
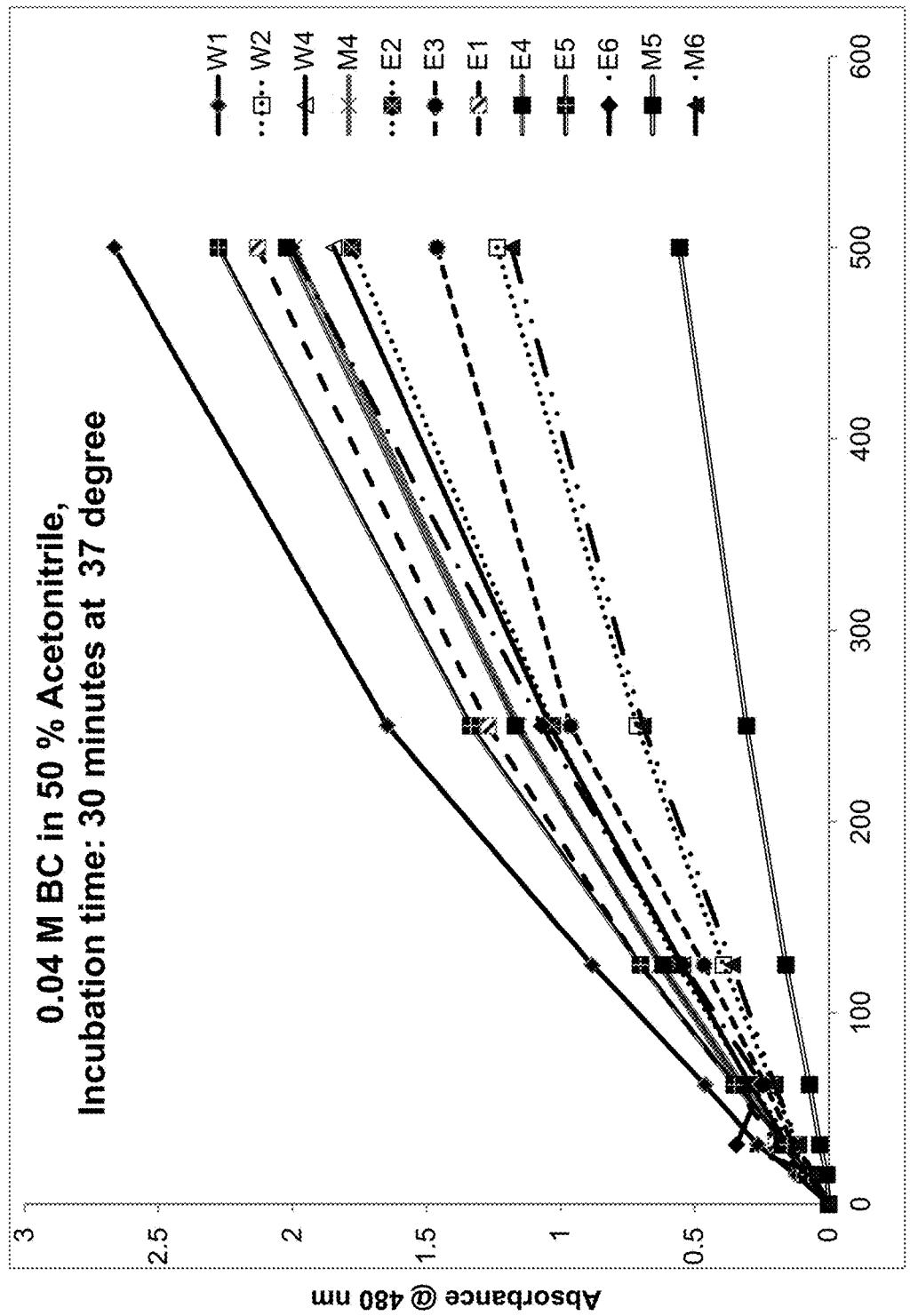

The variation range in signal intensity among different peptides was reasonable. Optimizations, such as using an organic solvent and/or higher incubation temperatures, further decreased variability. Other organic solvents and/or detergents such as SDS may also reduce variability. For example, as shown in FIG. 4, a range of various peptides were quantitated using 0.04 M bathocuproinedisulfonic acid disodium salt hydrate in water at 37° C., resulting in 39% variability. As shown in FIG. 5A, when the same peptides were quantitated using 0.04 M bathocuproinedisulfonic acid disodium salt hydrate in acetonitrile (an organic solvent) at 45° C., variability was reduced to 28%. The example shown in FIG. 5B shows the same peptides quantitated using 0.04 M bathocuproinedisulfonic acid disodium salt hydrate in 50% acetonitrile at 37° C. The method described herein provided less variability likely due to better solubilizing and better formulation of bathocuproine due to the presence of the disodium salt hydrate and optimized incubation conditions using an organic solvent and increased temperature. As an example, peptides that are hydrophobic add to variability; acetonitrile reduces variability possibly by reducing secondary and tertiary peptide structures and/or increasing peptide solubility.

Figure 6A:
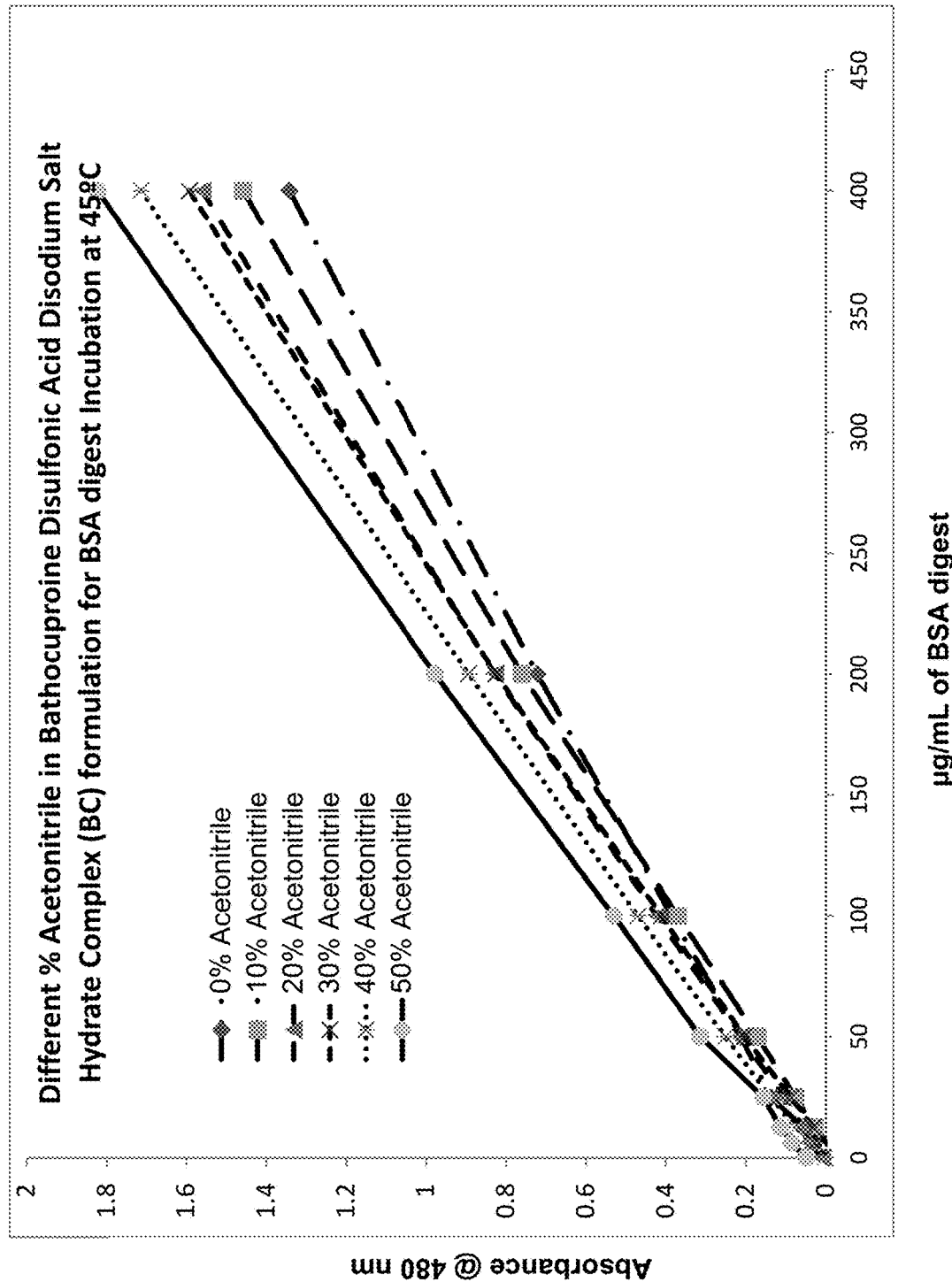
FIGS. 6A-B show effects of varying acetonitrile concentration using one embodiment of the methods provided herein with a BSA digest and HeLa digest.
Figure 6B:
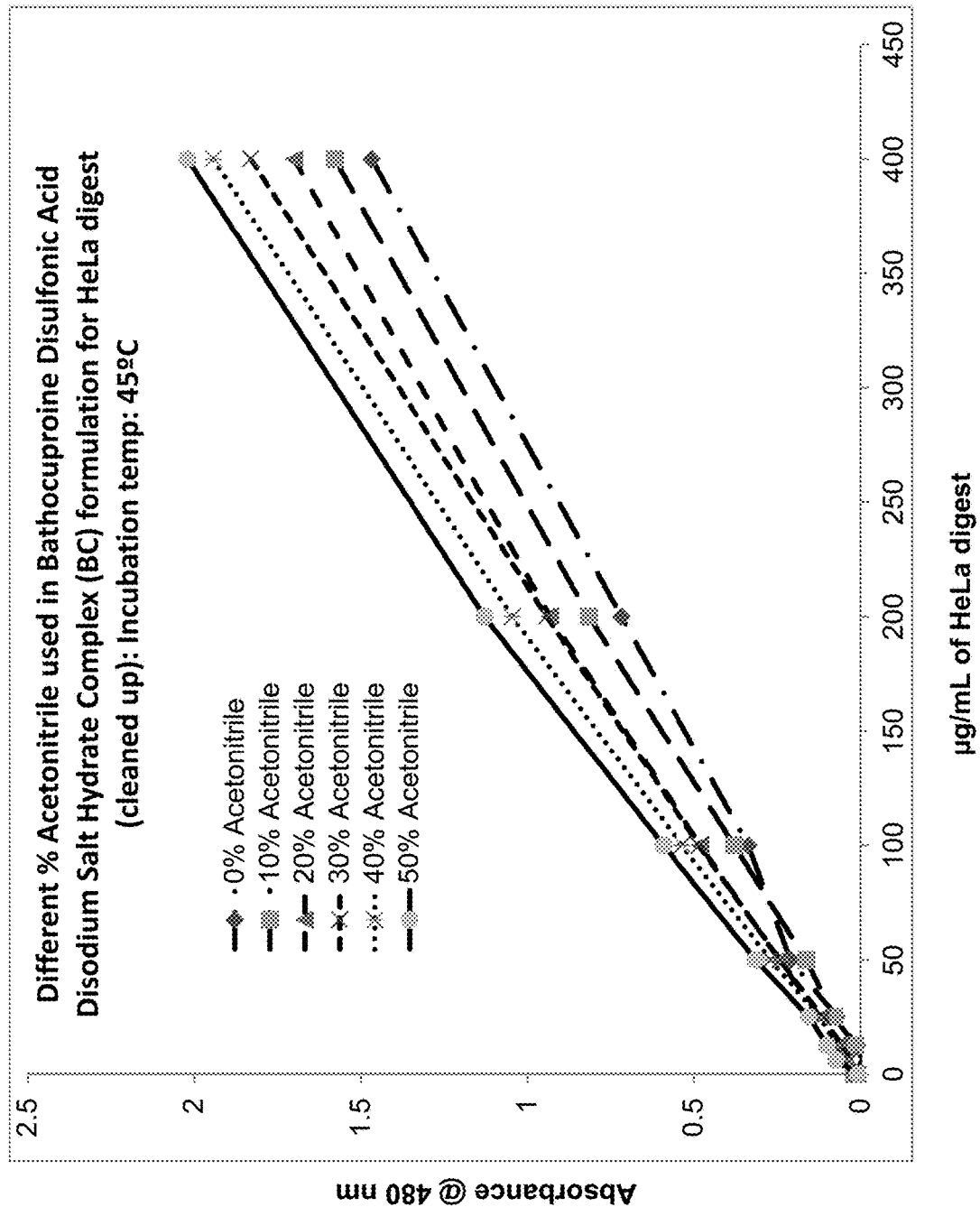

In one embodiment, the amount of acetonitrile in the assay composition was optimized. FIGS. 6A-B demonstrate the effect of varying amounts of acetonitrile in the methods provided herein. Acetonitrile concentrations ranging from 0% to 50% were used to prepare 0.04 M bathocuproinedisulfonic acid disodium salt hydrate solution. The formulations were then tested on different concentration of HeLa cell digest (15.6 µg/ml protein to 400 µg/ml protein) and BSA digest, which were incubated at 45° C. Both digests were prepared by reducing the appropriate protein with DTT, alkylated with IAA, blocked excess IAA with DTT, digested with trypsin, then cleaned up using a C18 column. As shown in FIGS. 6A-B, as the percentage of acetonitrile increased in the formulation, the S/N and assay sensitivity improved. There was 68% improvement between no acetonitrile in the bathocuproinedisulfonic acid disodium salt hydrate formulation and 50% acetonitrile in the bathocuproinedisulfonic acid disodium salt hydrate formulation.

Figure 7A:
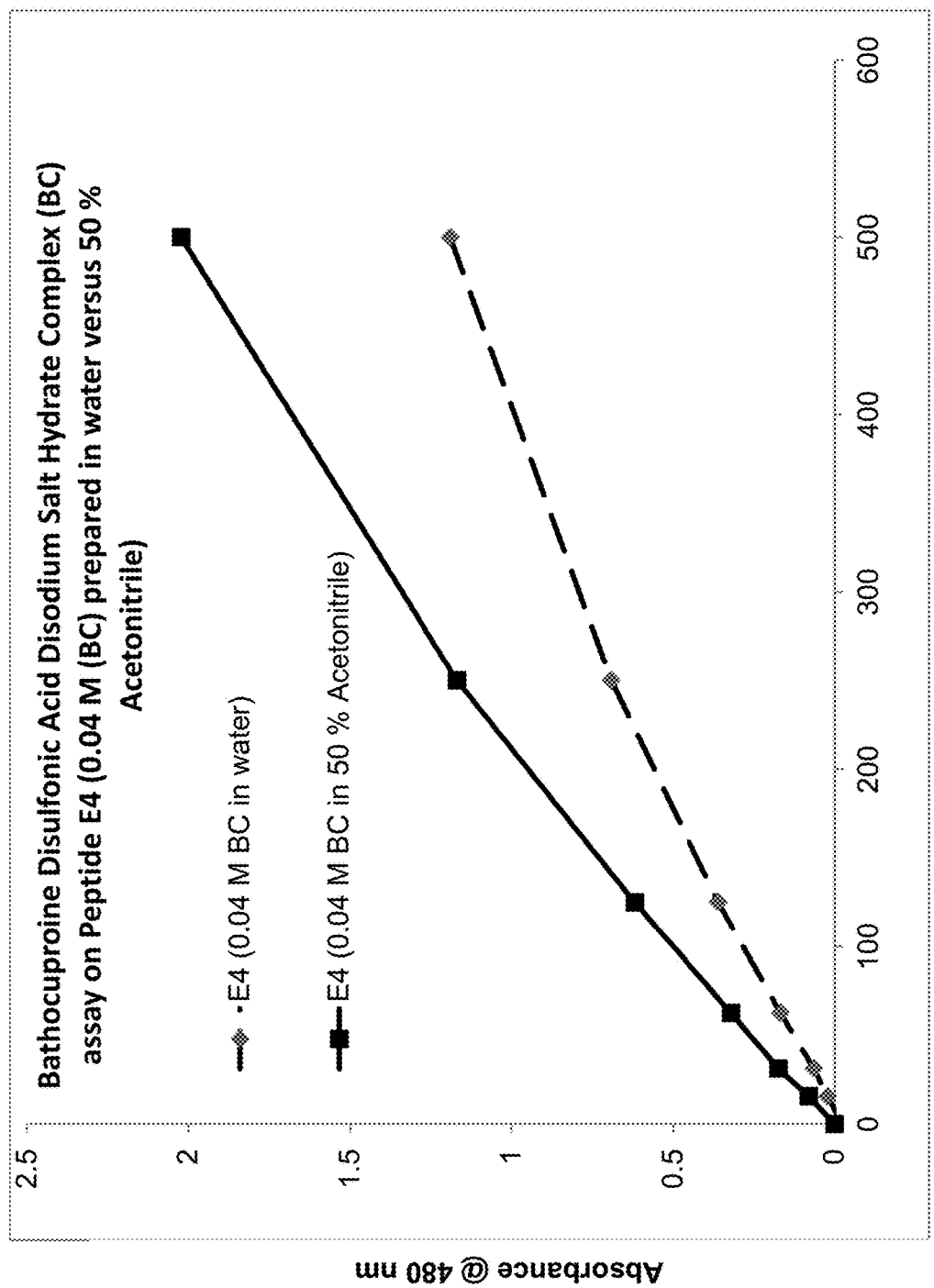
FIGS. 7A-B show effect of acetonitrile of measuring peptide concentration using certain embodiments of the methods provided herein.

The effect of acetonitrile in detecting single peptides using the method provided herein was evaluated. The results are shown in FIG. 7A for peptide E4 and in FIG. 7B for peptide E1. Two solutions (0.04 M bathocuproinedisulfonic acid disodium salt hydrate in 50% acetonitrile solution and 0.04 M bathocuproinedisulfonic acid disodium salt hydrate in water) were prepared. Thirteen peptides (data shown for peptides E4 and E1) were prepared with concentrations from 15.6 µg/ml to 500 µg/ml. Reagent solution (180 µl) was mixed with 20 µl peptide samples and incubated at 37° C. for 30 min.

Figure 7B:
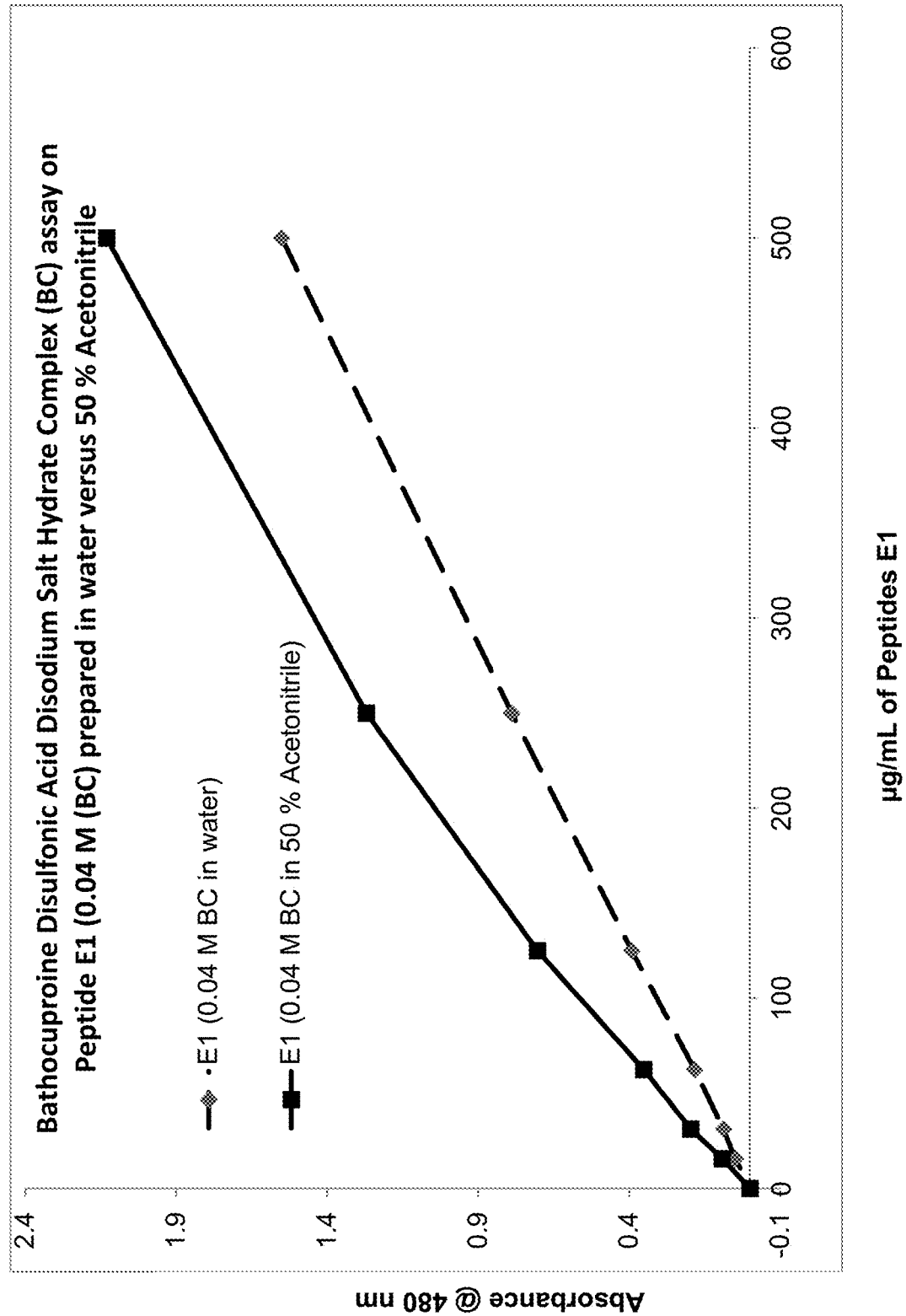

As shown in FIGS. 7A and 7B, the presence of acetonitrile in the formulation improved the S/N ratio and improved assay sensitivity. There was an average of 45% increase in signal intensity obtained with acetonitrile incorporated in the bathocuproinedisulfonic acid disodium salt hydrate formulation.

Figure 8:
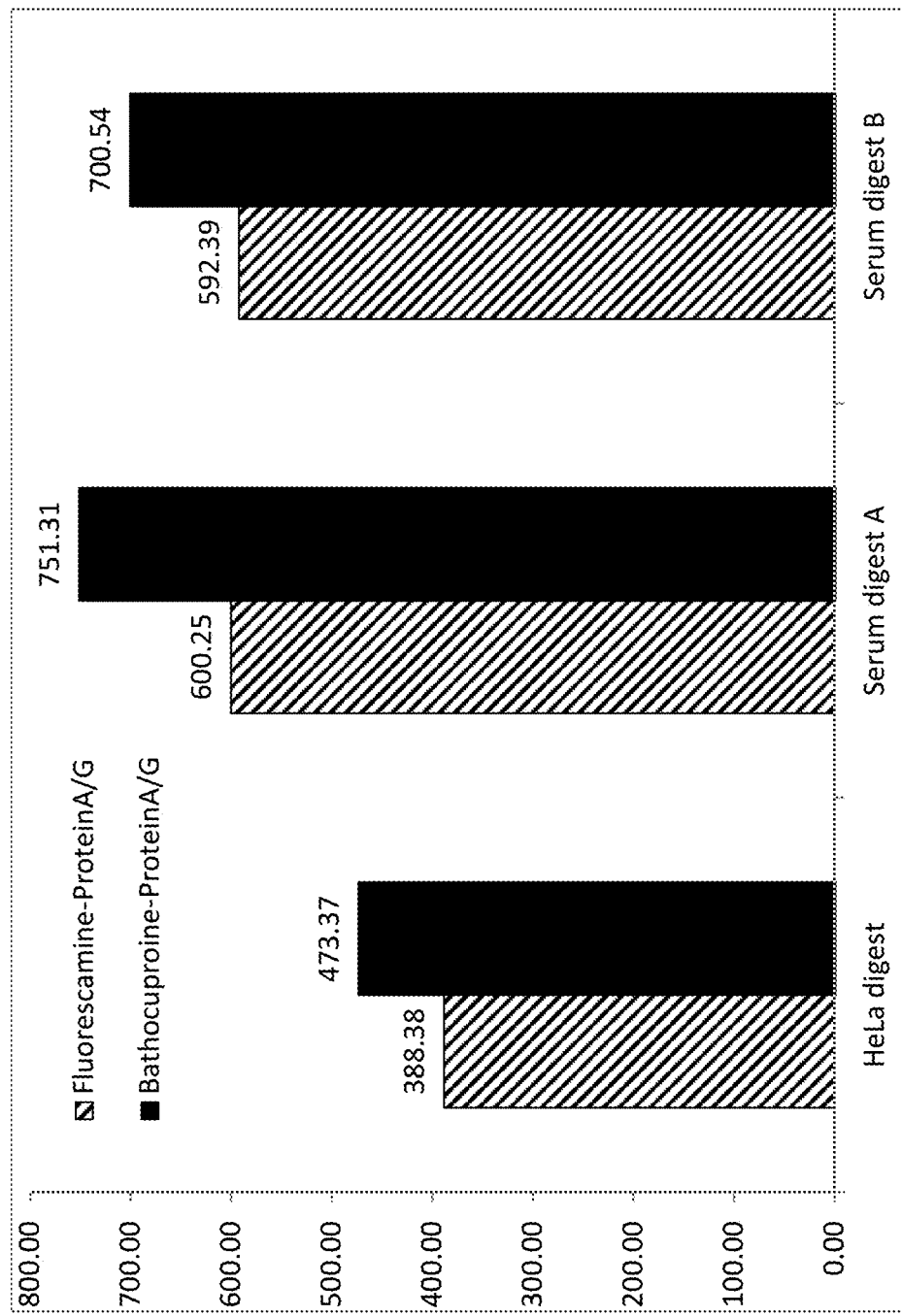
FIG. 8 shows peptide quantitation using an embodiment of the methods provided herein and a fluorescamine-based assay.

FIG. 8 shows the peptide concentration of three different protein digests using protein A/G to generate a standard curve. The results were extremely reproducible even using a fluorescamine assay, which measures peptide concentration by labeling the N-termini of peptides (*Thermo Scientific Nano Drop Protocol.* Fluorescamine Protein Assay 2008) and the present method using the same standards.

Figure 9A:
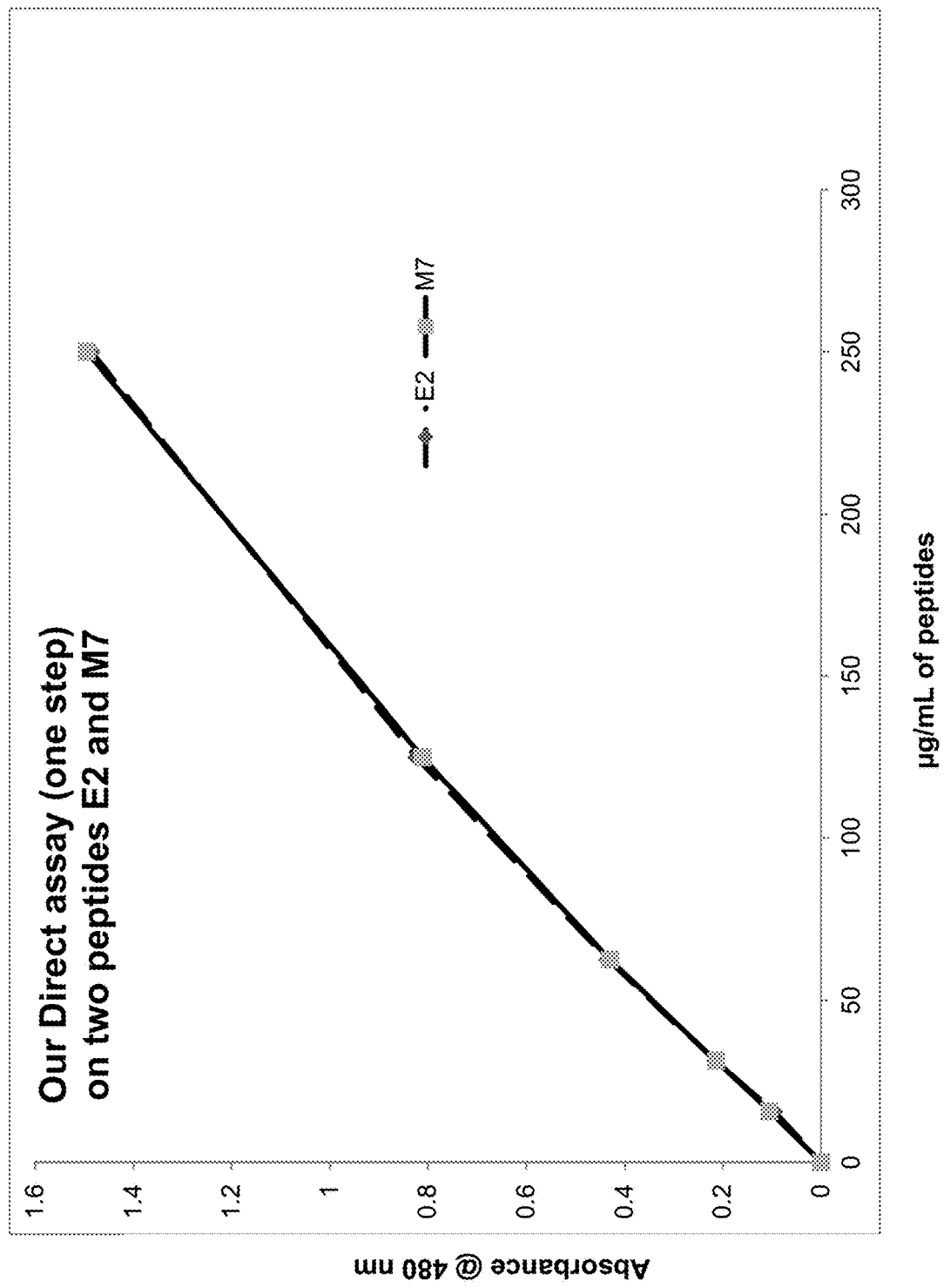
FIGS. 9A-B compares peptide quantitation using an embodiment of the methods provided herein and an indirect two-step method (Matsushita et al., Determination of Proteins by a Reverse Biuret Method Combined with the Copper-Bathocuproine Chelate Reaction. *Clinica Chimica Acta*. 216 (1993) 103-111).
Figure 9B:
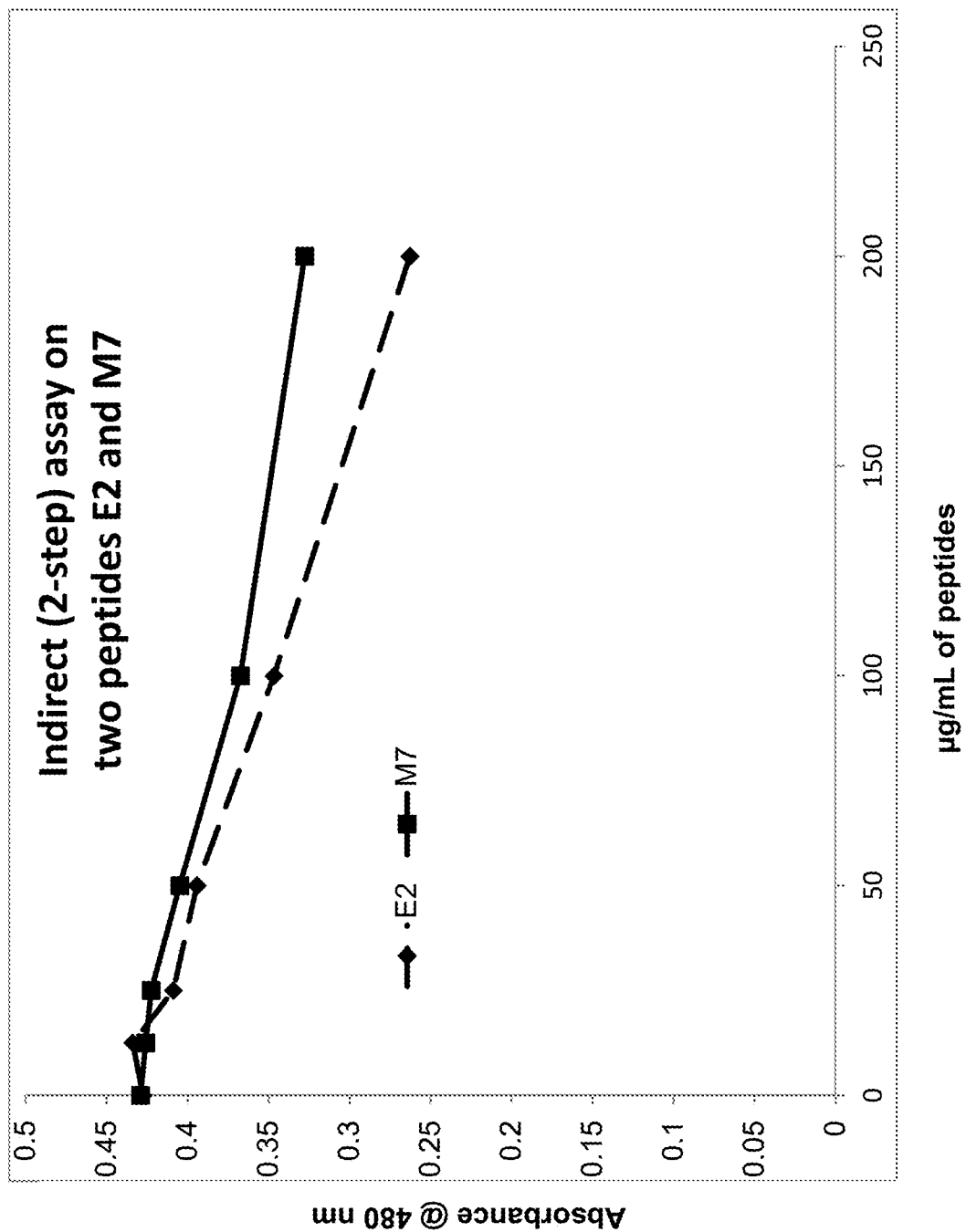

Results from the present method (FIG. 9A), a direct one-step method, were compared with the previously described indirect two-step method (FIG. 9B).

The present method used 0.04 M bathocuproinedisulfonic acid disodium salt hydrate in 50% acetonitrile-water mixture; the working solution was 0.48 bathocuproinedisulfonic acid disodium salt dehydrate solution:0.5 sodium tartrate solution:0.02 copper sulfate solution.

The indirect two-step method used ascorbic acid as reducing agent to reduce unreacted $Cu^{+2}$ to $Cu^{+1}$ and then subsequently chelate bathocuproine to $Cu^{+1}$. The amount of bathocuproine in the indirect two-step method was 0.8 mmol/liter, about 500 times lower than the concentration of bathocuproinedisulfonic acid disodium salt dehydrate in the present method. The two-step indirect method used a much higher assay total volume of 3 ml, compared to an assay total volume of 200 µl in the present method. A comparison of FIGS. 9A and 9B demonstrates that the present method showed more linearity and better sensitivity than the indirect two-step method.

Figure 10:
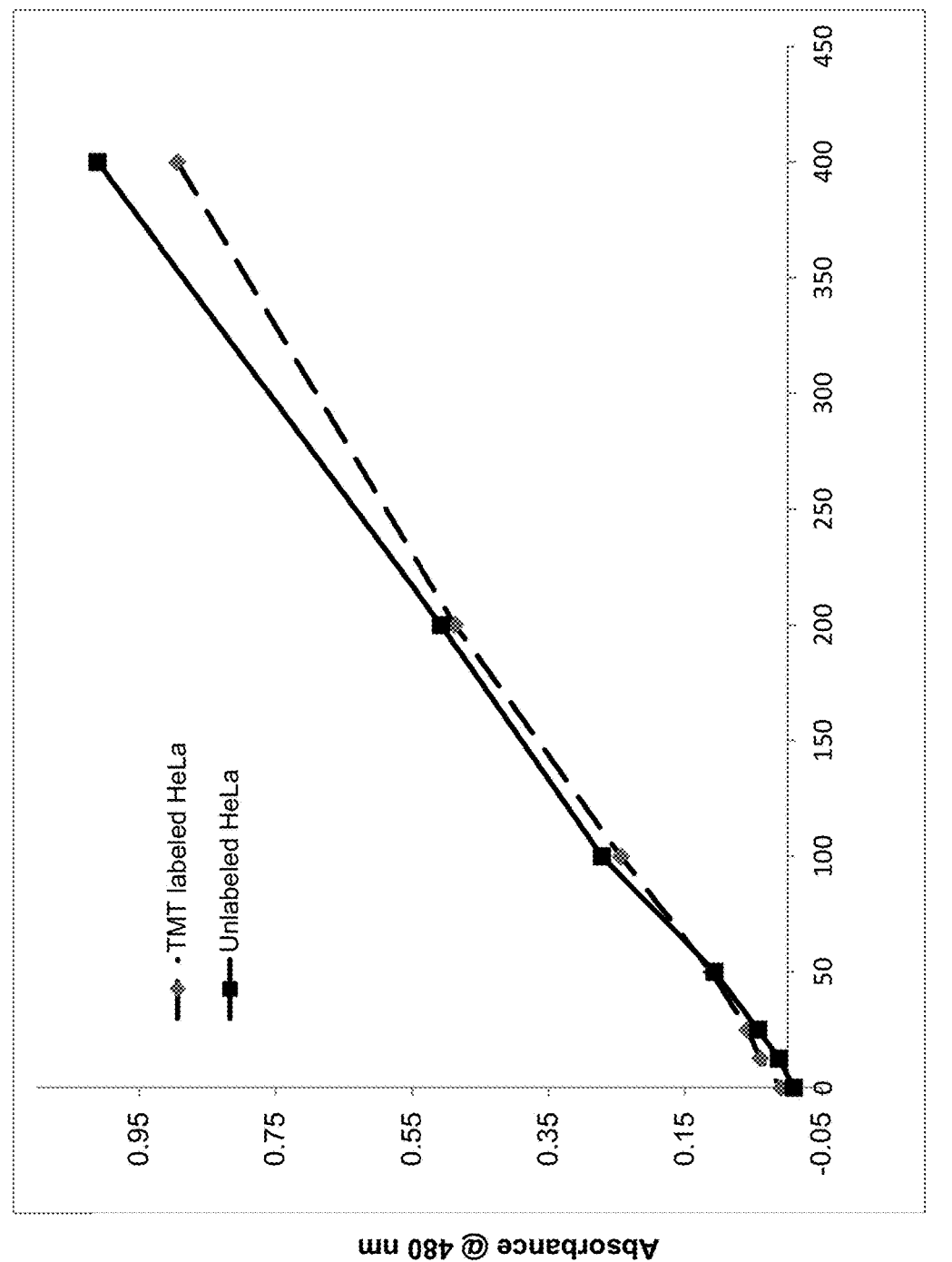
FIG. 10 demonstrates the ability of one embodiment of the methods provided herein to quantitate labeled peptides from a tryptic protein digest.

In certain embodiments, the methods provided herein may be used to quantitate labeled proteins and/or peptides. For example, labels used in MS, such as TMT, may be added to the protein or peptide. As shown in FIG. 10, the present method similarly detected and quantitated both TMT labeled and unlabeled HeLa digests. Because the methods provided herein are based on the reduction of copper, which is largely dependent on the peptide amide-backbone, they are not affected by peptide modifications such as TMT-labeling of amine groups. This is demonstrated in FIG. 10 showing identical responses for a TMT-labeled and unlabeled sample. This allows load/injection amounts of TMT-labeled samples to be standardized between MS analysis experiments improving results and consistency. The present method was also comparable with most digestion and solubilization reagents that are typically used in mass spectrometry analysis, such as triethylamine, urea, dithiothreitol, acetonitrile (shown in FIGS. 5A-B), formic acid, and trifluoroacetic acid.

Figure 11A:
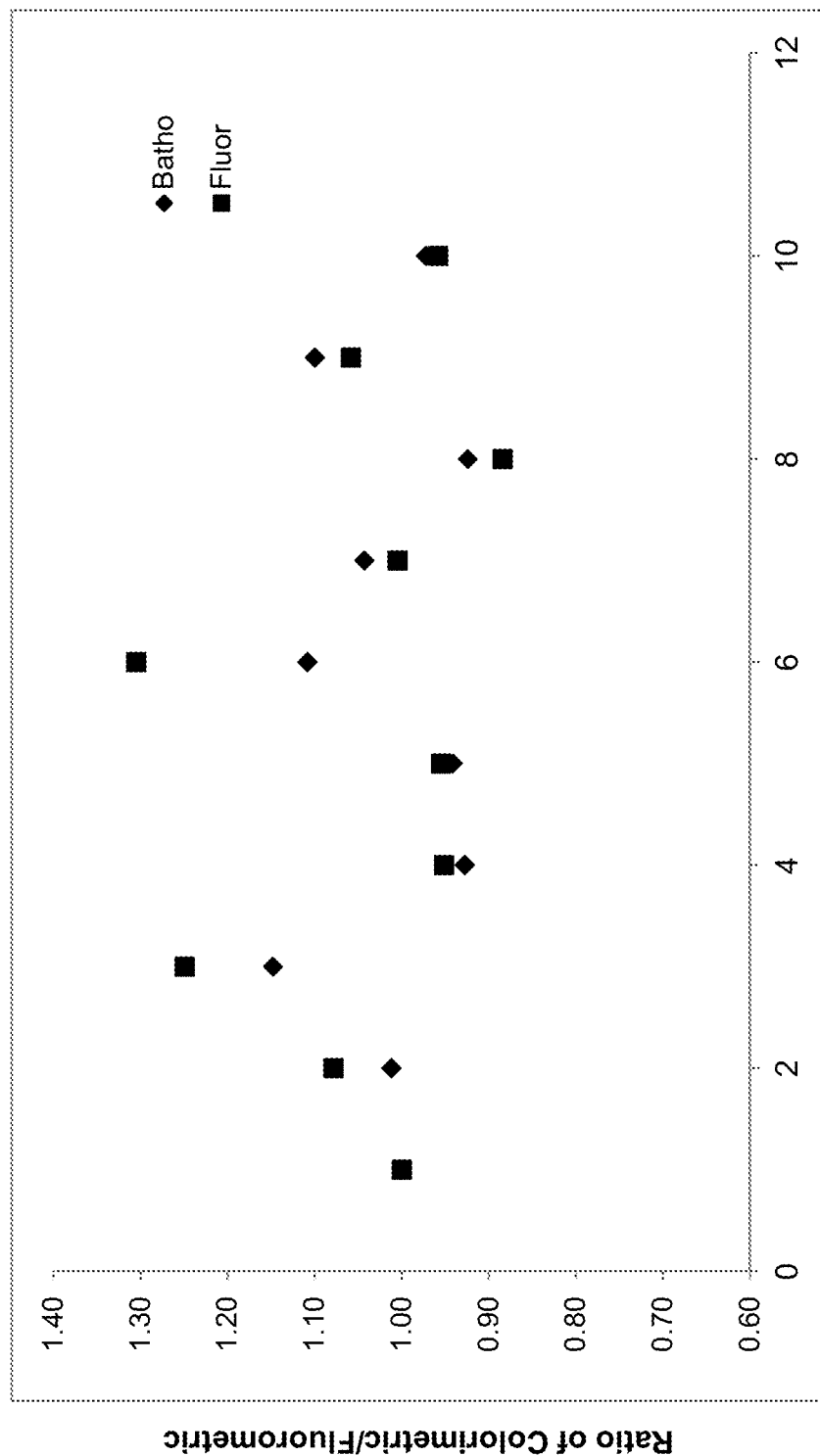
FIGS. 11A-B demonstrate quantitation of individual peptides or complex digests that can be used to aid in evaluation and normalization of samples before MS analysis.
Figure 11B:
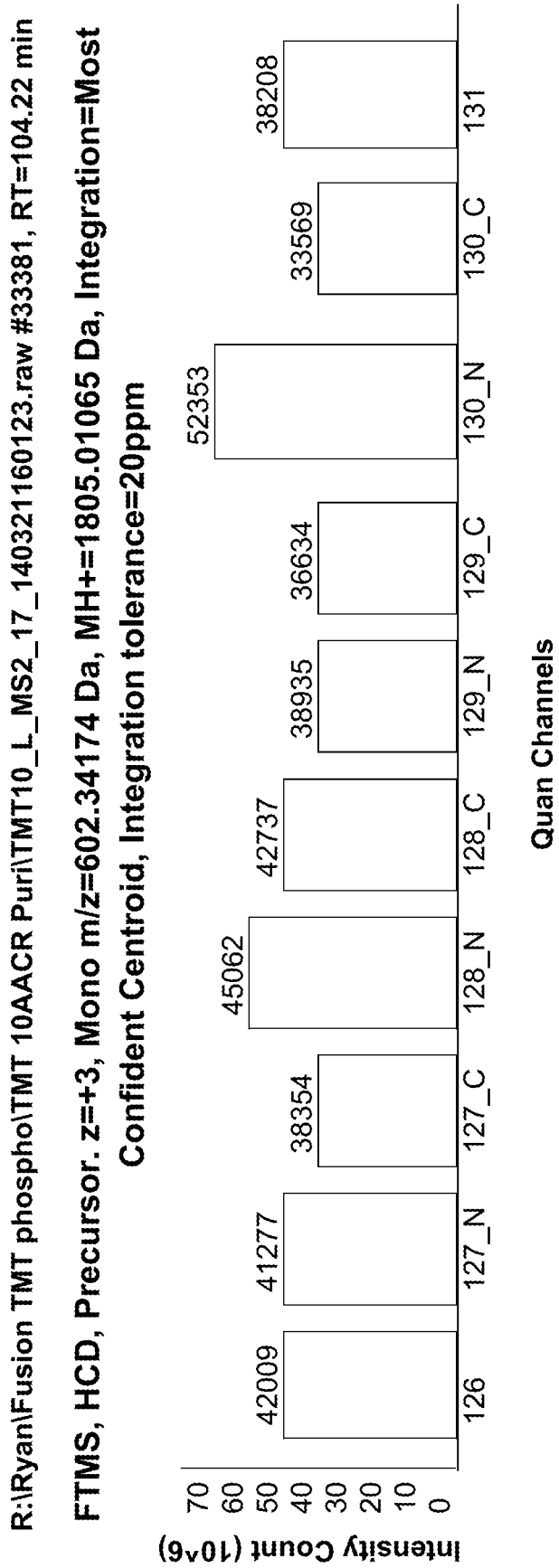

One embodiment provides a microplate assay for simple, reliable, and sensitive quantitation of individual peptides or complex digests that can be used to aid in evaluation and normalization of samples before MS analysis. Non-small lung carcinoma cell lines were treated with ten different sets of conditions, lysed, reduced, alkylated, and digested with trypsin before desalting using C18 columns. The concentration of each digest was then determined using the bathocuproine-based peptide assay according to the present teachings. The same results were generated using the fluorescamine-based assay (*Thermo Scientific Nanodrop Protocol.* Fluorescamine protein assay. 2008) as demonstrated in FIG. 11A. Each peptide sample concentration was then normalized before labeling individually with one of the Thermo Scientific TMT10PLEX™ Isobaric labeling reagents. Labeled samples were combined before peptide identification and relative quantitation using a Thermo Scientific ORBITRAP FUSION™ mass spectrometer. After normalization, non-regulated peptides displayed ratios of 1:1:1:1:1:1:1:1:1:1 despite complex sample handling and preparation, as shown in FIG. 11B.

The methods described herein provided enhanced sensitivity and flexibility compared to current methods, making them an excellent tool for determining and monitoring the concentration of peptide samples. They required a relatively small sample volume (10 µl-20 µl), yet still providing excellent sensitivity with a working peptide concentration range of 25 µg/ml-1000 µg/ml. They are useful tools for monitoring in common MS applications, e.g., they are peptide amide-backbone dependent allowing for the quantitation of both labeled and unlabeled peptides.

The embodiments shown and described herein are only specific embodiments and are not limiting in any way. Therefore, various changes, modifications, or alterations to those embodiments may be made without departing from the spirit of the invention in the scope of the following claims. The references cited are expressly incorporated by reference herein in their entirety.

What is claimed is:

1. A direct method for determining peptide or protein concentration in a sample, the method for determining peptide or protein concentration comprising
   (a) combining the sample with a quantitation assay reagent composition comprising copper sulfate, acetonitrile present at a concentration ranging from about 10% to about 50%, and a complex to form a mixture, wherein the complex contains the formula:

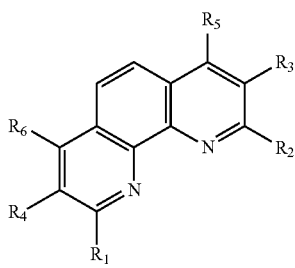

wherein
      each of $R_1$ and $R_2$ is independently chosen from $C_1$-$C_6$ straight and branched alkyls, and $C_6$-$C_{20}$ aryl, alkylaryl, and arylalkyls;
      each of $R_3$ and $R_4$ is independently chosen from the group consisting of hydrogen; a sulfonate salt chosen from a salt of sodium, potassium, and lithium; a phosphonate salt chosen from a salt of sodium, potassium, and lithium; and a carboxylate salt chosen from a salt of sodium, potassium, and lithium; and
      each of $R_5$ and $R_6$ is

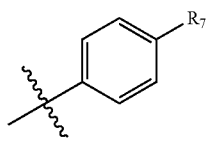

wherein $R_7$ is independently chosen from the group consisting of hydrogen; sulfonate salts chosen from sodium, potassium, and lithium; phosphonate salts chosen from sodium, potassium, and lithium; and carboxylate salts chosen from sodium, potassium, and lithium; with the proviso that at least one of $R_3$, $R_4$, and $R_7$ is not H;
   (b) incubating the mixture under conditions sufficient to form a colored complex; and
   (c) measuring absorbance of the colored complex at a wavelength ranging from 450 nm to 500 nm, wherein the amount of colored complex measured is directly proportional to peptide or protein concentration in the sample.

2. The method of claim 1, wherein the reagent composition in (a) further comprises tartrate and sodium bicarbonate.

3. The method of claim 1, further comprising, after step (c), determining the peptide or protein concentration in the sample by comparing the measured absorbance of step (c) with an absorbance of at least one sample containing a known concentration of a standard, wherein the absorbance of the at least one sample containing a known concentration is measured at a wavelength ranging from 450 nm to 500 nm.

4. The method of claim 3, wherein the standard comprises at least one entity chosen from peptides, peptide mixtures, and peptide digests at a known concentration.

5. The method of claim 1, wherein the incubation conditions are chosen from a range of from room temperature to about 45° C.; a range of from about 19° C. to about 22° C.; about 37° C.; and about 45° C.

6. The method of claim 5, wherein the incubation conditions range from about 19° C. to about 22° C.

7. The method of claim 6, wherein the incubation conditions are about 37° C.

8. The method of claim 1, wherein mass spectrometry analysis of the sample is performed after step (c).

9. The method of claim 1, wherein the quantitation assay reagent composition comprises bathocuproinedisulfonic acid disodium salt hydrate with about 50% acetonitrile.

10. A direct method for determining peptide or protein concentration in a sample, the method for determining peptide or protein concentration comprising
    (a) combining the sample with a quantitation assay reagent composition comprising copper sulfate, acetonitrile present at a concentration ranging from about 10% to about 50%, and a complex to form a mixture, wherein the complex contains bathocuproinedisulfonic acid disodium salt hydrate:

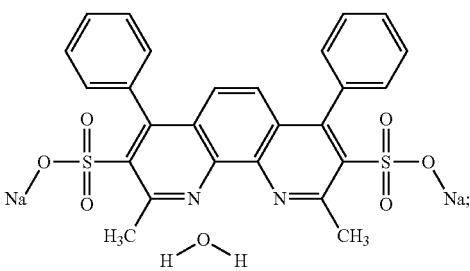

(b) incubating the mixture under conditions sufficient to form a colored complex; and
    (c) measuring absorbance of the colored complex at a wavelength ranging from 450 nm to 500 nm, wherein the amount of colored complex measured is directly proportional to peptide or protein concentration in the sample.

11. The method of claim 10, further comprising, after step (c), determining the peptide or protein concentration in the sample by comparing the measured absorbance of step (c) with an absorbance of at least one sample containing a known concentration of a standard, wherein the absorbance of the at least one sample containing a known concentration is measured at a wavelength ranging from 450 nm to 500 nm.

12. The method of claim 11 where the standard comprises at least one entity chosen from peptides, peptide mixtures, and peptide digests at a known concentration.

13. The method of claim 10, wherein the reagent composition in (a) further comprises tartrate.

14. The method of claim 10, wherein the reagent composition in (a) further comprises sodium bicarbonate.

15. The method of claim 13, wherein the tartrate is sodium tartrate.

16. The method of claim 10, wherein the incubation conditions range from room temperature to about 45° C.

17. The method of claim 16, where the incubation conditions range from about 19° C. to about 22° C.

18. The method of claim 16, where the incubation conditions are about 37° C.

19. The method of claim 10, wherein the sample volume ranges from about 5 µl to about 20 µl.

20. The method of claim 10, wherein the sample comprises a plurality of peptides.

21. The method of claim 10, wherein the absorbance is measured by an automated microplate reader.

22. The method of claim 10, wherein the sample is in at least one additional solvent chosen from aqueous solvents and organic solvents.

23. The method of claim 10, further comprising, after step (c), analyzing the sample by mass spectrometry.

24. The method of claim 10, wherein the quantitation assay reagent composition further comprises at least one component chosen from detergents and additional organic solvents.

25. A direct method for determining peptide or protein concentration in a sample, the method comprising
(a) combining the sample with a quantitation assay reagent composition comprising
50% acetonitrile and
a complex containing bathocuproinedisulfonic acid disodium salt hydrate:

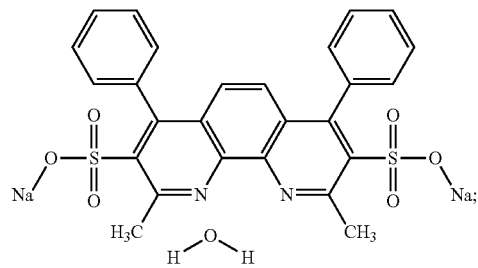

(b) incubating the mixture under conditions sufficient to form a colored complex; and
(c) measuring absorbance of the colored complex at a wavelength ranging from 450 nm to 500 nm, wherein the amount of colored complex measured is directly proportional to peptide or protein concentration in the sample.

26. The method of claim 25, further comprising, after step (c), determining the peptide or protein concentration in the sample by comparing the measured absorbance of step (c) with an absorbance of at least one sample containing a known concentration of a standard, wherein the absorbance of the at least one sample containing a known concentration is measured at a wavelength ranging from 450 nm to 500 nm.

27. The method of claim 25, wherein the reagent composition in step (a) further comprises tartrate and copper sulfate.

28. The method of claim 25, further comprising, after step (c), analyzing the sample by mass spectrometry.

29. The method of claim 26, wherein the standard comprises at least one entity chosen from peptides, peptide mixtures, and peptide digests at a known concentration.

* * * * *

SEQUENCE LISTING

<160> NUMBER OF SEQ ID NOS: 22

<210> SEQ ID NO 1
<211> LENGTH: 12
<212> TYPE: PRT
<213> ORGANISM: Artificial Sequence

```
<220> FEATURE:
<223> OTHER INFORMATION: /note="Description of Artificial Sequence:
      Synthetic peptide"

<400> SEQUENCE: 1

His Ser Asp Ala Val Phe Thr Asp Asn Tyr Thr Arg
1               5                   10

<210> SEQ ID NO 2
<211> LENGTH: 12
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 2

Asp Ala Glu Phe Arg His Asp Ser Gly Tyr Glu Val
1               5                   10

<210> SEQ ID NO 3
<211> LENGTH: 9
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 3

Asp Ala Glu Phe Arg His Asp Ser Cys
1               5

<210> SEQ ID NO 4
<211> LENGTH: 13
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 4

Asp Ala Glu Phe Arg His Asp Ser Gly Tyr Glu Val His
1               5                   10

<210> SEQ ID NO 5
<211> LENGTH: 10
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 5

Ser Glu Val Lys Met Asp Ala Glu Phe Arg
1               5                   10

<210> SEQ ID NO 6
<211> LENGTH: 17
<212> TYPE: PRT
<213> ORGANISM: Artificial Sequence
<220> FEATURE:
<223> OTHER INFORMATION: /note="Description of Artificial Sequence:
      Synthetic peptide"
```

<400> SEQUENCE: 6

Ser Tyr Ser Met Glu His Phe Arg Trp Gly Lys Pro Val Gly Lys Lys
1               5                   10                  15

Arg

<210> SEQ ID NO 7
<211> LENGTH: 14
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 7

Phe Arg His Asp Ser Gly Tyr Glu Val His His Gln Lys Leu
1               5                   10

<210> SEQ ID NO 8
<211> LENGTH: 12
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 8

Lys Phe His Glu Lys His His Ser His Arg Gly Tyr
1               5                   10

<210> SEQ ID NO 9
<211> LENGTH: 11
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 9

Tyr Thr Asp Ile Glu Met Asn Arg Leu Gly Lys
1               5                   10

<210> SEQ ID NO 10
<211> LENGTH: 14
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 10

Glu Phe Arg His Asp Ser Gly Tyr Glu Val His His Gln Lys
1               5                   10

<210> SEQ ID NO 11
<211> LENGTH: 16
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 11

Asp Ala Glu Phe Arg His Asp Ser Gly Tyr Glu Val His His Gln Lys
1               5                   10                  15

```
<210> SEQ ID NO 12
<211> LENGTH: 16
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 12

Arg Gln Ile Lys Ile Trp Phe Gln Asn Arg Arg Met Lys Trp Lys Lys
1               5                   10                  15

<210> SEQ ID NO 13
<211> LENGTH: 9
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 13

Ile Leu Arg Gly Ser Val Ala His Lys
1               5

<210> SEQ ID NO 14
<211> LENGTH: 20
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 14

Met Glu Val Gly Trp Tyr Arg Ser Pro Phe Ser Arg Trp His Leu Tyr
1               5                   10                  15

Arg Asn Gly Lys
            20

<210> SEQ ID NO 15
<211> LENGTH: 10
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 15

Ser Tyr Ser Met Glu His Phe Arg Trp Gly
1               5                   10

<210> SEQ ID NO 16
<211> LENGTH: 11
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 16

Ile Ser Arg Pro Pro Gly Phe Ser Pro Phe Arg
1               5                   10

<210> SEQ ID NO 17
<211> LENGTH: 13
<212> TYPE: PRT
<213> ORGANISM: Artificial Sequence
```

```
<220> FEATURE:
<223> OTHER INFORMATION: /note="Description of Artificial Sequence:
      Synthetic peptide"

<400> SEQUENCE: 17

Asn Val Ile Gln Ile Ser Asn Asp Leu Glu Asn Leu Arg
1               5                   10

<210> SEQ ID NO 18
<211> LENGTH: 11
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 18

Tyr Glu Val His His Gln Lys Leu Val Phe Phe
1               5                   10

<210> SEQ ID NO 19
<211> LENGTH: 6
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 19

Lys Lys Pro Tyr Ile Leu
1               5

<210> SEQ ID NO 20
<211> LENGTH: 8
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 20

Ser Ile Ile Asn Phe Glu Lys Leu
1               5

<210> SEQ ID NO 21
<211> LENGTH: 12
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 21

Gly Gly Phe Leu Arg Arg Ile Arg Pro Lys Leu Lys
1               5                   10

<210> SEQ ID NO 22
<211> LENGTH: 11
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 22

Val Phe Phe Ala Glu Asp Val Gly Ser Asn Lys
1               5                   10
```